United States Patent [19]
Washizuka et al.

[11] Patent Number: 5,423,848
[45] Date of Patent: Jun. 13, 1995

[54] TROCAR

[75] Inventors: Nobuhiko Washizuka; Yasuhiko Oomagari; Tsuruo Hatori; Tsuyoshi Tsukagoshi; Minoru Tsuruta; Seiji Kuramoto; Shuichi Kimura; Akio Nakada; Shiro Bito; Shinichi Nishigaki; Kenji Yoshino; Keisuke Saito; Yasuo Goto, all of Tokyo, Japan

[73] Assignee: Olympus Optical Co., Ltd., Tokyo, Japan

[21] Appl. No.: 254,495

[22] Filed: Jun. 6, 1994

Related U.S. Application Data
[63] Continuation of Ser. No. 45,354, Apr. 8, 1993.

[30] Foreign Application Priority Data

| Apr. 14, 1992 | [JP] | Japan | 4-094472 |
| Apr. 14, 1992 | [JP] | Japan | 4-094475 |
| Apr. 14, 1992 | [JP] | Japan | 4-094477 |
| Apr. 15, 1992 | [JP] | Japan | 4-095596 |
| Apr. 15, 1992 | [JP] | Japan | 4-095597 |
| Apr. 15, 1992 | [JP] | Japan | 4-095598 |
| Sep. 17, 1992 | [JP] | Japan | 4-247978 |
| Dec. 9, 1992 | [JP] | Japan | 4-329419 |

[51] Int. Cl.$^6$ .................................. A61B 17/00
[52] U.S. Cl. .................................. 606/185; 606/41; 606/45; 606/167; 604/164; 604/264; 604/167
[58] Field of Search .................. 606/34–48, 606/167, 184, 185; 604/21, 22, 164, 264, 156, 157, 158, 167

[56] References Cited

U.S. PATENT DOCUMENTS

| 3,595,239 | 7/1971 | Petersen | 606/45 |
| 3,964,487 | 6/1976 | Judson | 606/39 |
| 4,550,727 | 11/1985 | Rexroth | 606/39 |
| 4,580,562 | 4/1986 | Goof et al. | 606/39 |
| 4,682,981 | 7/1987 | Suzuki et al. | |
| 4,788,977 | 12/1988 | Farin et al. | 606/39 |
| 4,793,345 | 12/1988 | Lehmer | 606/39 |
| 4,807,620 | 2/1989 | Stul et al. | 606/45 |
| 4,986,814 | 1/1991 | Burney et al. | 604/164 |
| 5,053,016 | 10/1991 | Lander | |
| 5,066,288 | 11/1991 | Deniega | |
| 5,104,383 | 4/1992 | Shichman | |
| 5,221,281 | 6/1993 | Klicek | 606/45 |

FOREIGN PATENT DOCUMENTS

WO04632 3/1993 WIPO .................. 606/185

Primary Examiner—Peter A. Aschenbrenner
Attorney, Agent, or Firm—Frishauf, Holtz, Goodman & Woodward

[57] ABSTRACT

A trocar comprises an obturator having a piercing tip, and a cannula for forming a passage in tissue that is punched by the piercing tip. The cannula is formed from a flexible tube or a coil tube and transforms and libitum in accordance with the shape of the surgical tool that is to be inserted into the body cavity through the cannula. Therefore, the trocar of the invention allows insertion of a surgical tool curved in a circular arc into the body cavity without requiring no enlargement of the inside diameter of the cannula.

4 Claims, 25 Drawing Sheets

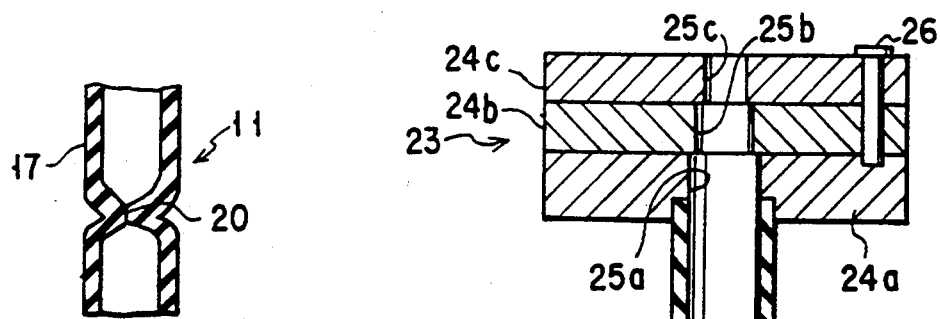
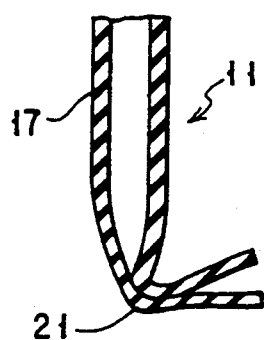
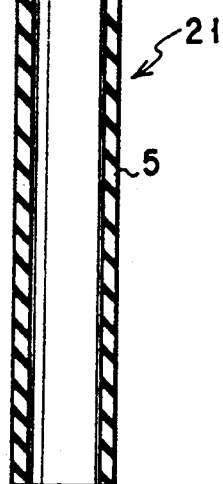
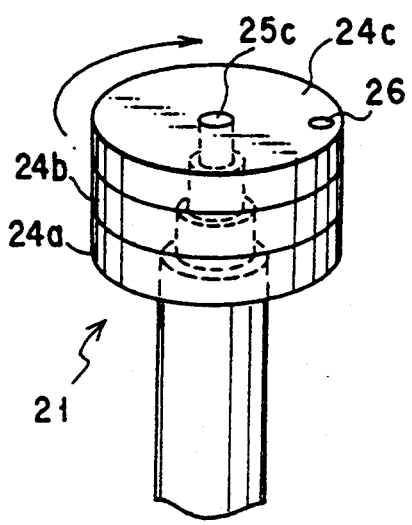
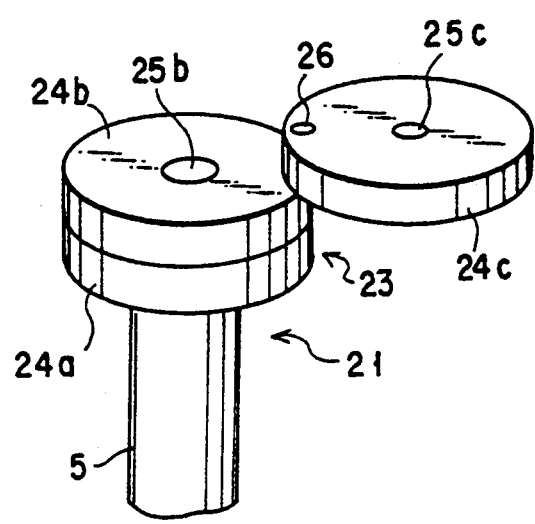
F I G. 6
F I G. 7
F I G. 8
F I G. 9
F I G. 10

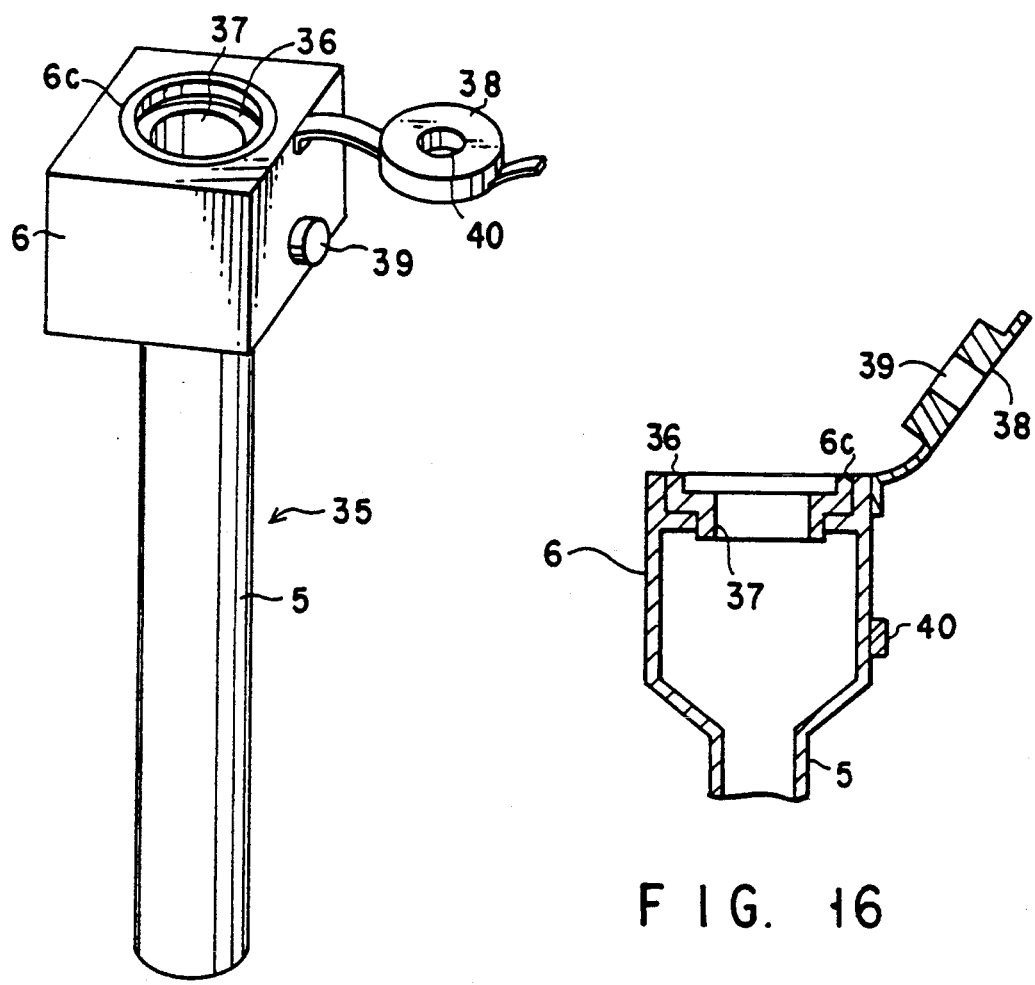
FIG. 15
FIG. 16
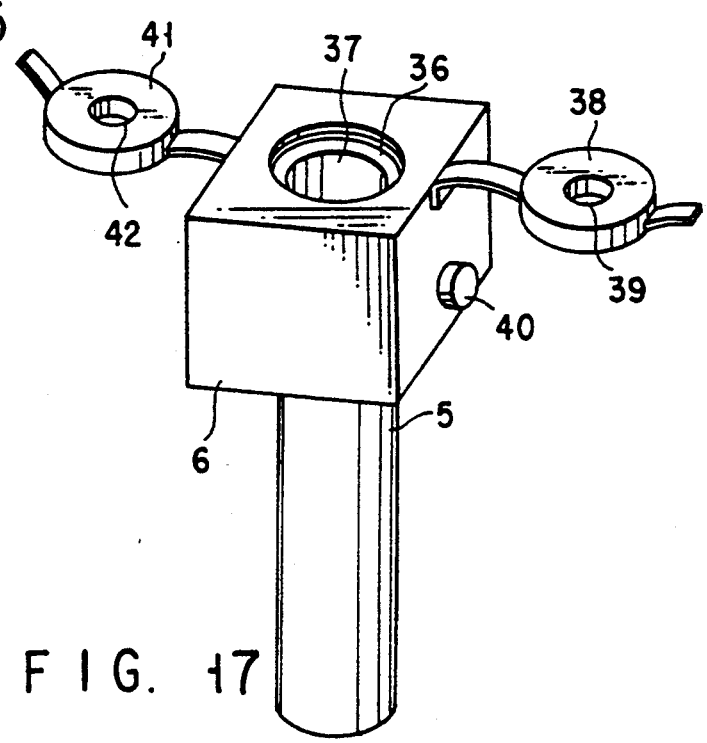
FIG. 17

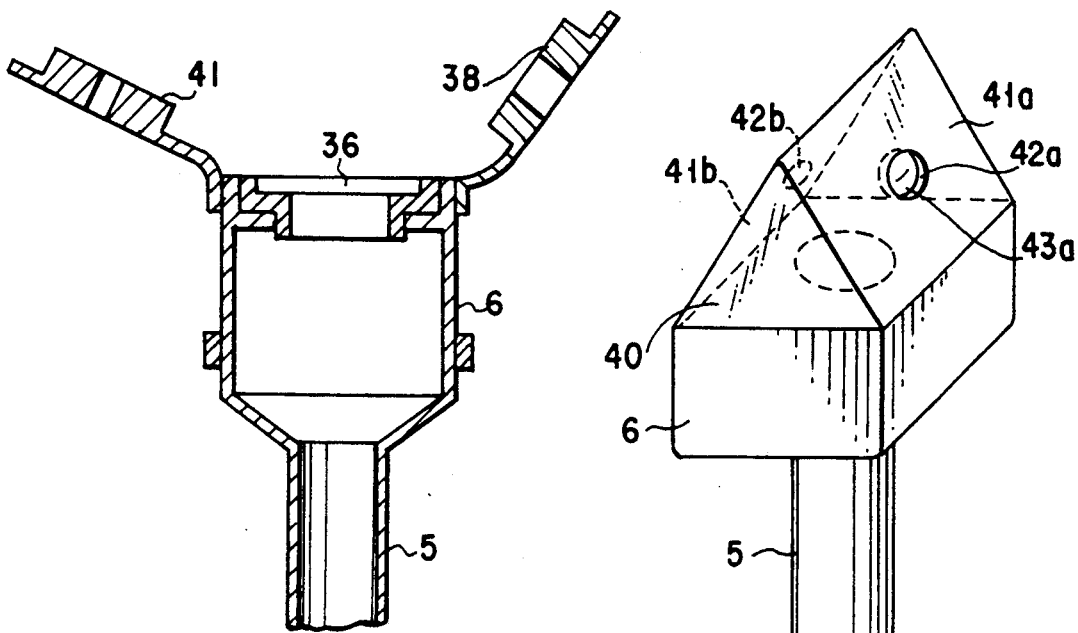
FIG. 18
FIG. 19
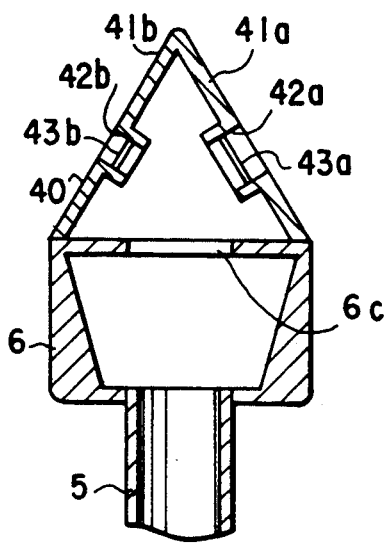
FIG. 20
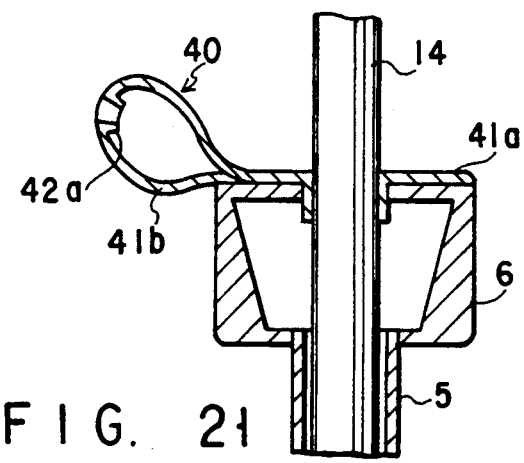
FIG. 21

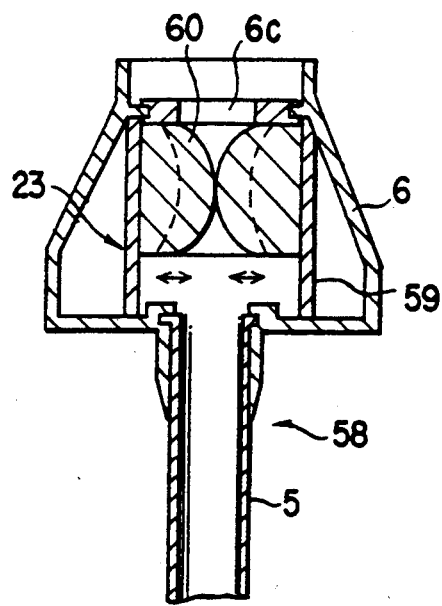
F I G. 24a
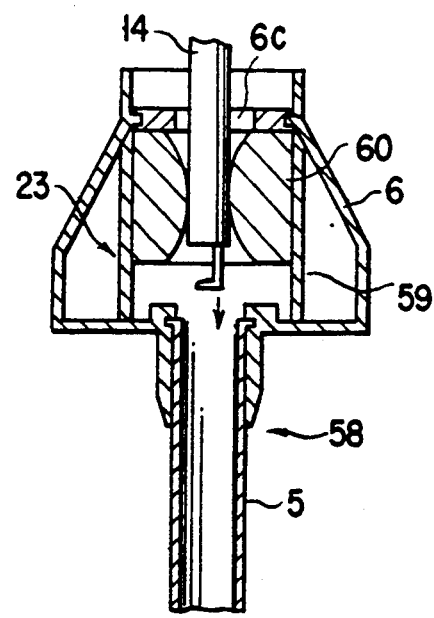
F I G. 24b
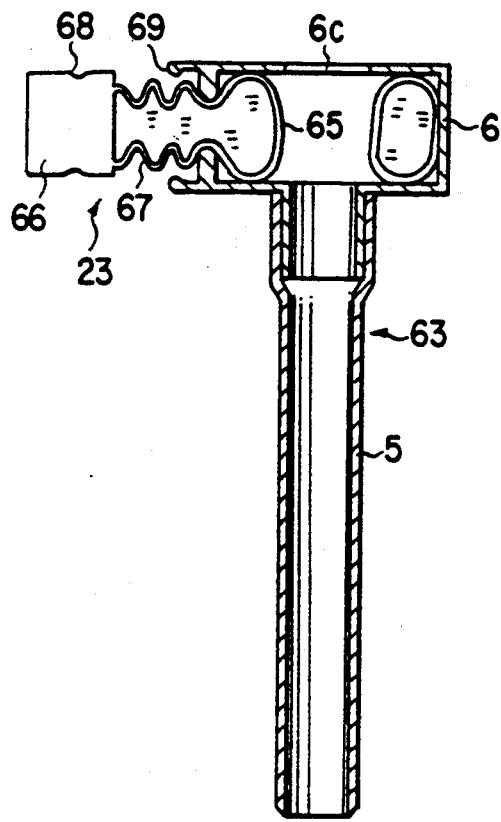
F I G. 25a
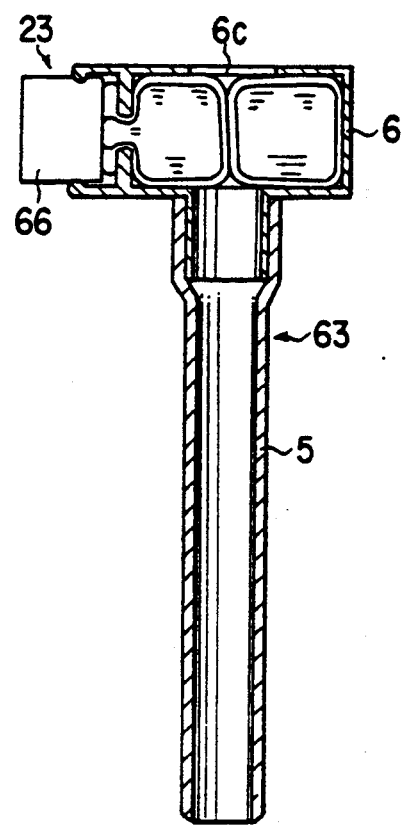
F I G. 25b

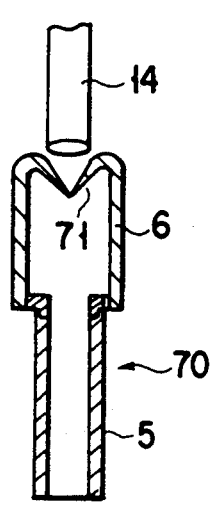
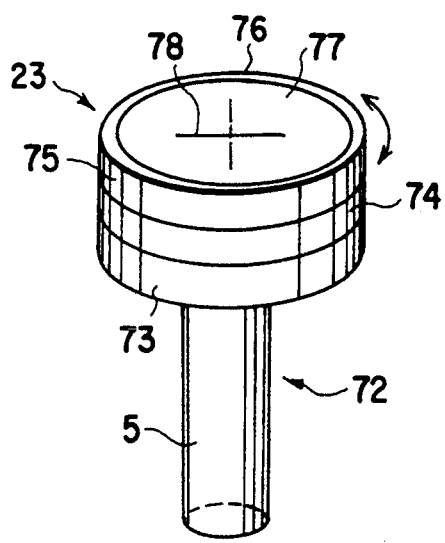
FIG. 26  FIG. 27
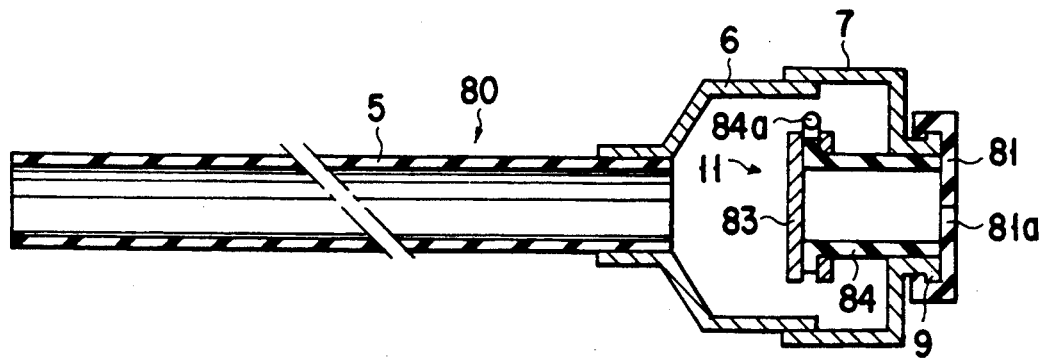
FIG. 28
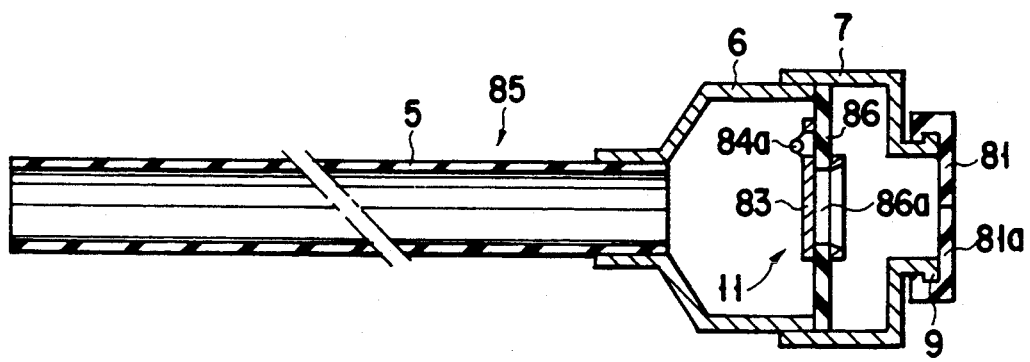
FIG. 29

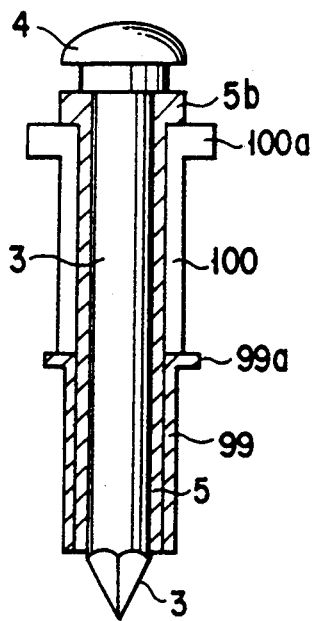
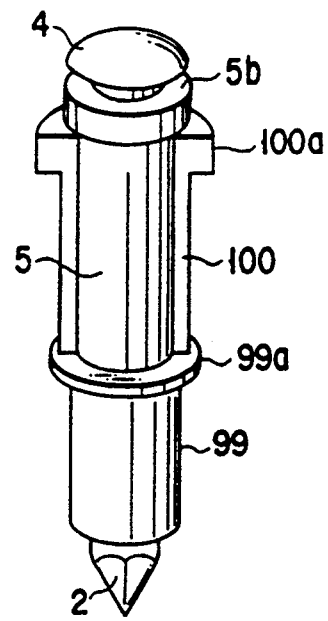
FIG. 38   FIG. 39
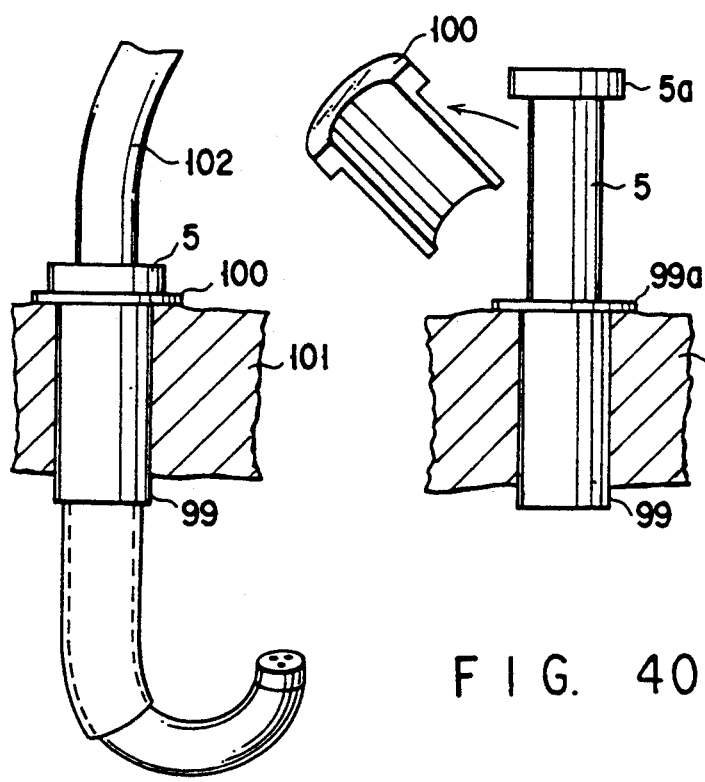
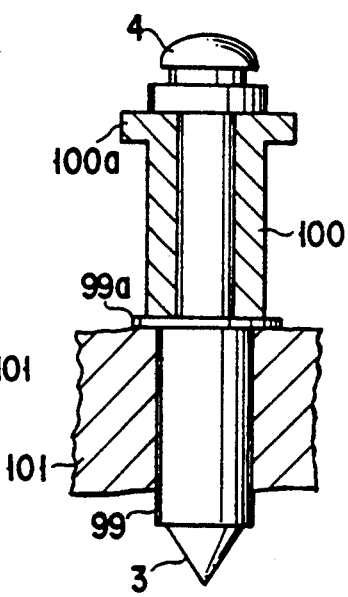
FIG. 40b   FIG. 40a
FIG. 40c

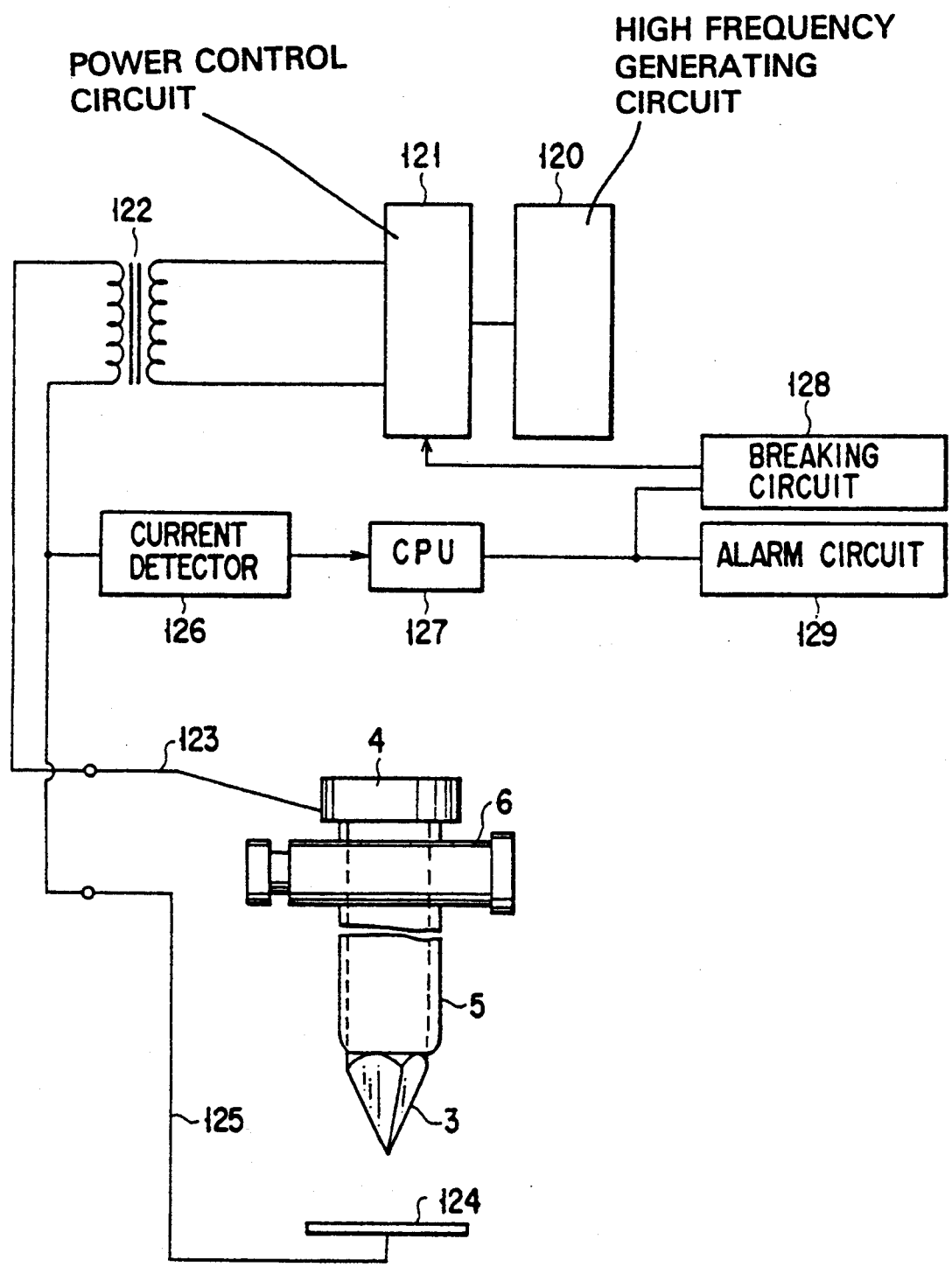
F I G. 43

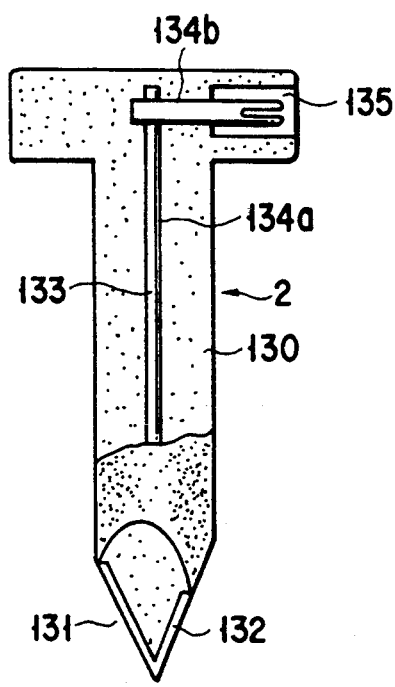
FIG. 52
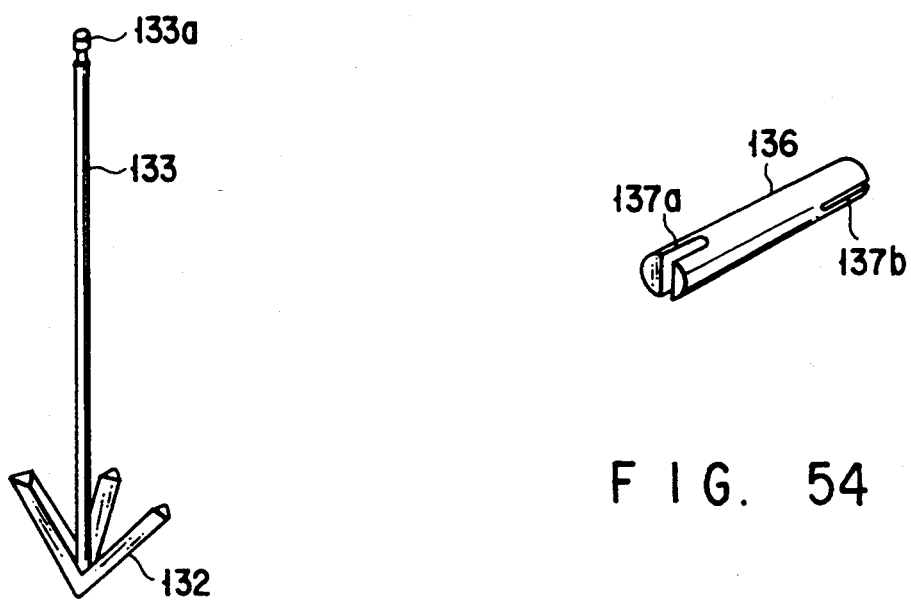
FIG. 53
FIG. 54

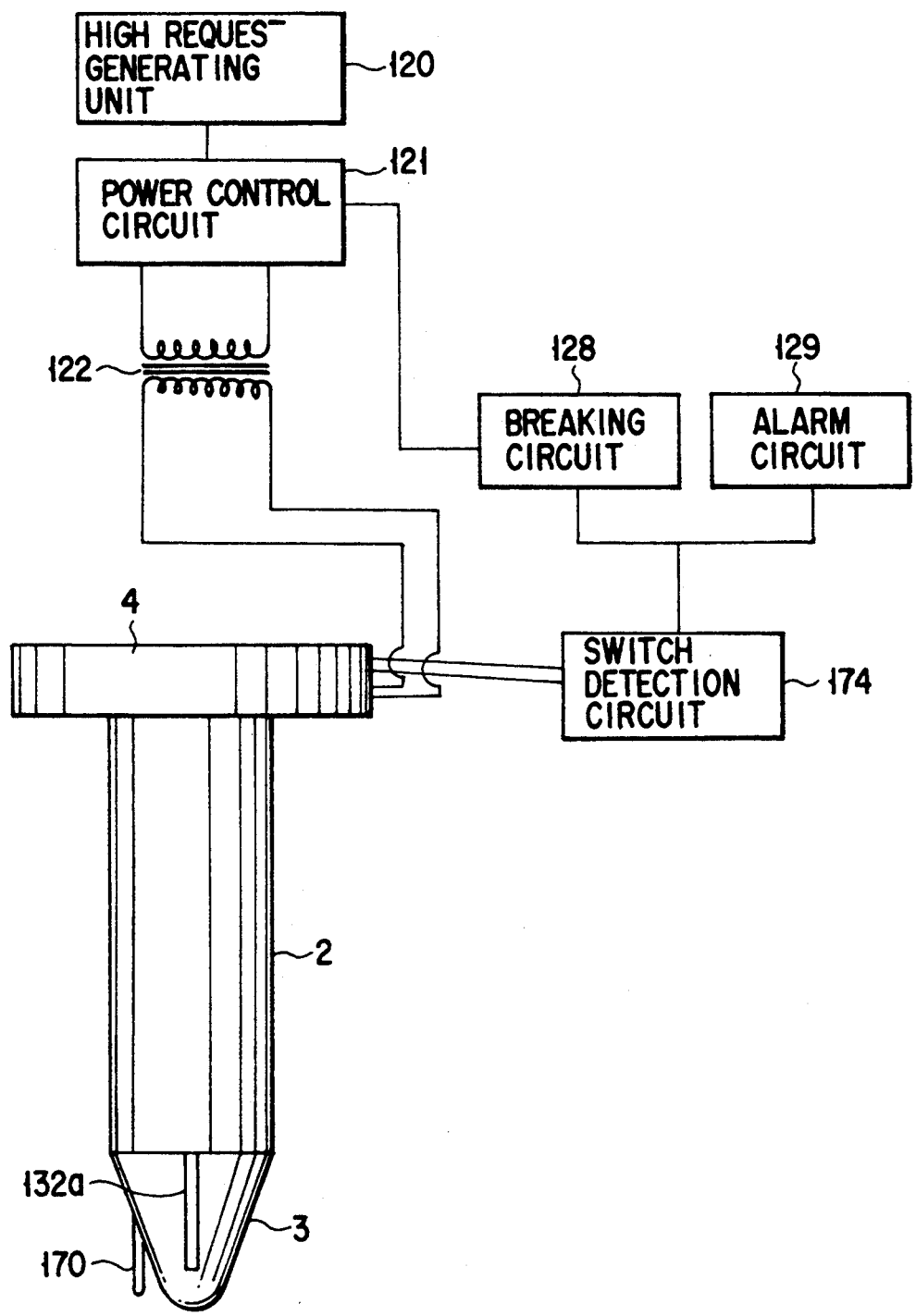
F I G. 55

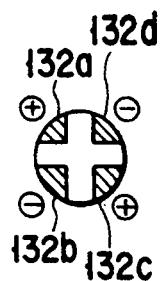 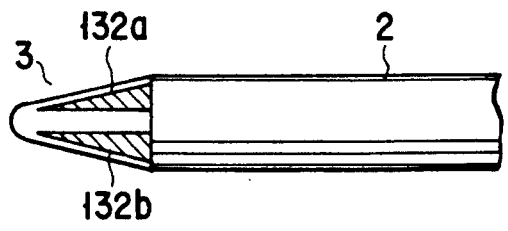
F I G. 58a    F I G. 58b
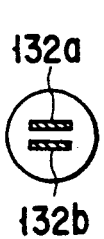 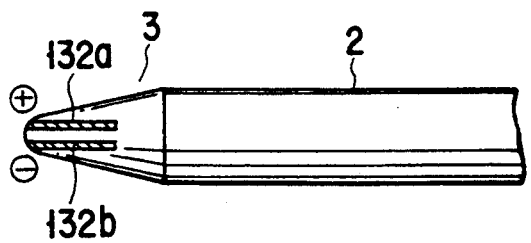
F I G. 59a    F I G. 59b
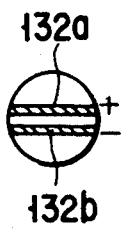 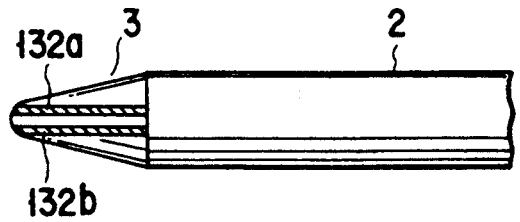
F I G. 60a    F I G. 60b

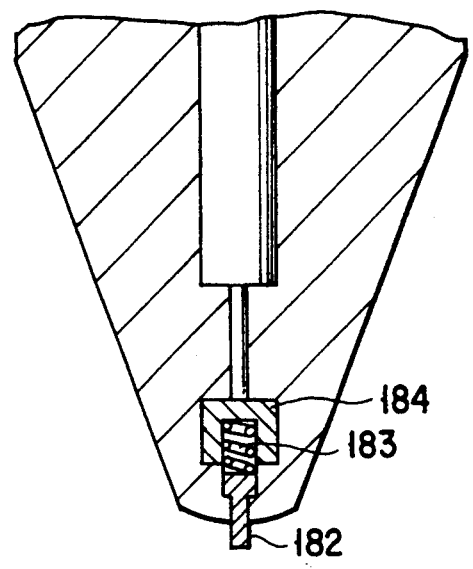
F I G. 63
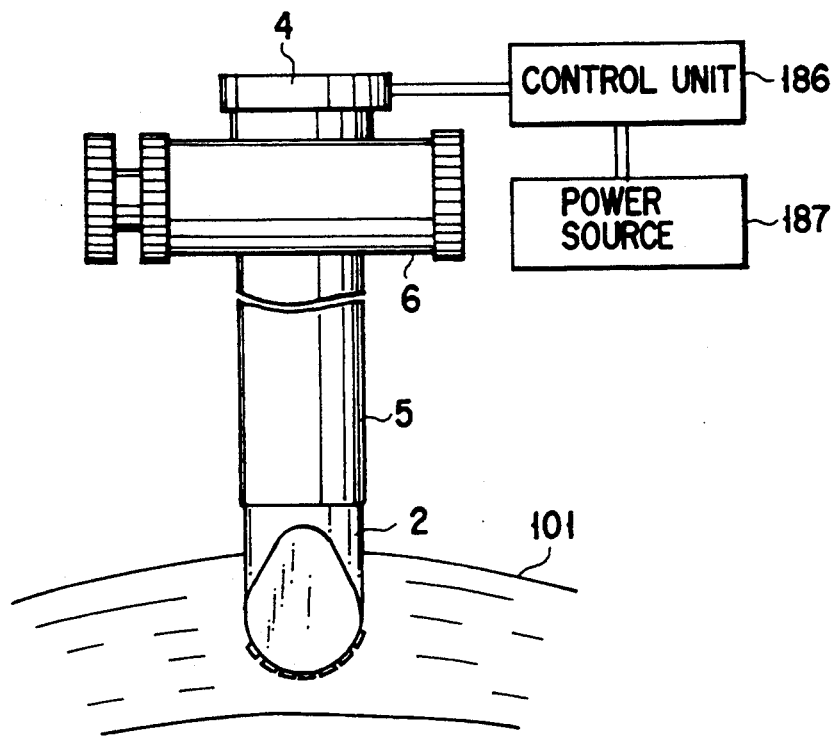
F I G. 64a

TROCAR

This application is a Continuation of application Ser. No. 08/045,354, filed Apr. 8, 1993.

BACKGROUND OF THE INVENTION

1. Field of the Invention

This invention relates to a trocar used to form a hole in a body cavity during performance of thoracoscopic surgery or performance of laparoscopic surgery.

2. Description of the Related Art

A trocar generally comprises an obturator and a cannula. The obturator has a pyramid-shaped piercing tip at one end, and moves the piercing tip into tissue to form a hole to provide access to a body cavity. On the other hand, the cannula is located around the obturator. The cannula is inserted into the body cavity together with the obturator through the hole formed by the piercing tip. Such a trocar, therefore, forms a pathway in the inside of the cannula for inserting an endoscope or a surgical tool into the body cavity, by extracting or withdrawing the obturator from the cannula inserted into the body cavity.

When thoracoscopic surgery of the pneumothorax is required, the obturator and the cannula are inserted into a thoracic cavity through the patient's chest bones. Then, the obturator is extracted from the cannula, the surgical tool is inserted into the thoracic cavity through the cannula, and the surgical tool is brought near to the patient's lungs for performance of the pneumothorax treatment. In this case, it is difficult to get the surgical tool to approach to the back side of the lungs if the pneumothorax-inducing bulla is at the back side of the lungs.

When the bulla is at the back side of the lungs, therefore, it is desirable to use a surgical tool curved in a circular arc. But insertion of such a surgical tool into the thoracic cavity requires that the inside diameter of the cannula be formed to be larger than in prior art cannulas, since the cannula is formed in a straight shape and is formed of rigid materials such as stainless steel (see U.S. Pat. No. 5,053,016, U.S. Pat. No. 5,104,383). However, the insertion of the cannula into the thoracic cavity through the chest bones is difficult when the inside diameter of the cannula be formed to be larger than in the prior art cannulas.

SUMMARY OF THE INVENTION

The objective of the invention is to provide a trocar capable of inserting surgical tools curved in a circular arc into a body cavity through a cannula without the necessity of forming the inside diameter of the cannula larger than before.

Another objective of the invention is to provide a trocar capable of inserting not only surgical tools curved in a circular arc but also straight shaped surgical tools into the body cavity through the cannula.

For the attainment of these objectives, the trocar of this invention is arranged so that the cannula has a flexible tube or a coil tube. Therefore the cannula can conform its shape in accordance with the shape of surgical tool to be inserted into the body cavity through the cannula.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 3b is a sectional view of the housing shown in FIG. 3a;

FIGS. 6 and 7 are schematic views showing modification examples of the seal device shown in FIG. 4;

FIG. 8 is a sectional view of the trocar schematically showing a fourth embodiment of the invention;

FIGS. 9 and 10 are external views of the seal device shown in FIG. 8;

FIG. 15 is a external view showing a seventh embodiment of the invention;

FIG. 16 is a sectional view of the housing of the cannula assembly shown in FIG. 15;

FIGS. 17 and 18 are schematic views showing modification examples of the cannula assembly shown in FIG. 15;

FIG. 19 is a schematic view showing an eighth embodiment of the invention;

FIGS. 20 and 21 are sectional views of the housing shown in FIG. 19;

FIGS. 24a and 24b are sectional views showing a tenth embodiment of the invention;

FIGS. 25a and 25b are sectional views showing an eleventh embodiment of the invention;

FIG. 26 is a sectional views showing a twelfth embodiment of the invention;

FIG. 27 is a external view showing a thirteenth embodiment of the invention;

FIG. 28 is a sectional view schematically showing a fourteenth embodiment of the invention;

FIG. 29 is a sectional view showing a fifteenth embodiment of the invention;

FIGS. 38 and 39 are drawings showing the trocar of an eighteenth embodiment of the invention;

FIGS. 40a, 40b and 40c are drawings to explain the actions of the trocar shown in FIG. 38;

FIG. 43 is a schematic view showing a twentieth embodiment of the invention;

FIGS. 52, 53 and 54 are drawings showing a third modification example of the obturator shown in FIG. 46;

FIGS. 55, 56 and 57 are drawings showing a fourth modification example of the obturator shown in FIG. 46;

FIGS. 58a and 58b are drawings showing a fifth modification example of the obturator shown in FIG. 46;

FIGS. 59a and 59b are drawings showing a sixth modification example of the obturator shown in FIG. 46.

FIGS. 60a and 60b are drawings showing a seventh modification example of the obturator shown in FIG. 46;

FIG. 63 is a sectional view taken on line C—C of FIG. 62;

FIGS. 64a, 64b and 64c are drawings to explain the action of the trocar shown in FIG. 61;

DETAILED DESCRIPTION OF THE PREFERRED EMBODIMENTS

Figure 1:
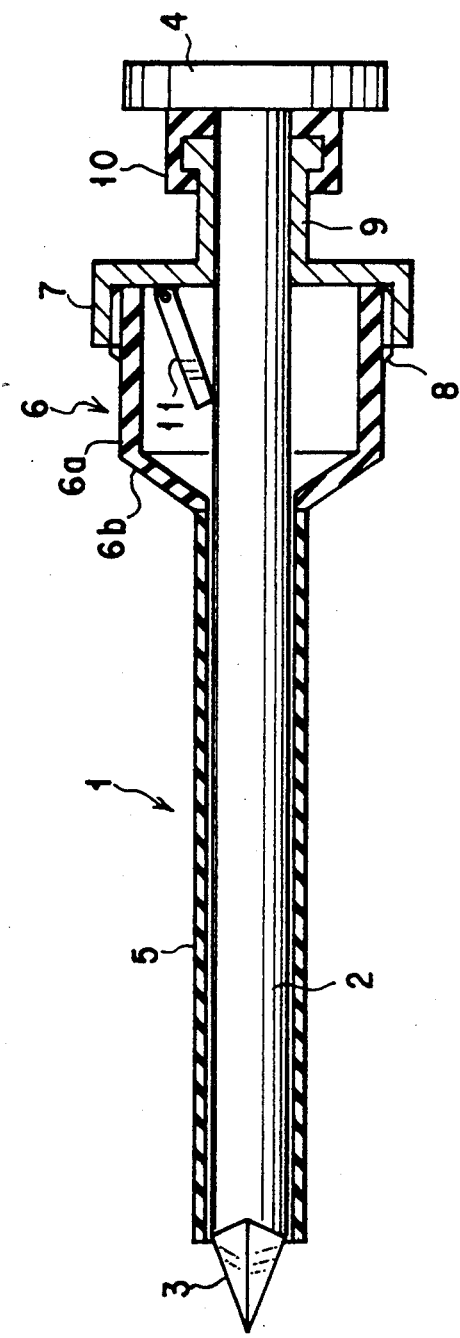
FIG. 1 is a sectional view of the trocar schematically showing a first embodiment of the invention.

FIG. 1 shows the construction of the trocar of a first embodiment of the invention. The trocar 1 comprises an obturator 2 and a cannula 5. The obturator 2 is formed of stainless steel or other rigid materials, has a piercing tip 3 for pinking in a body cavity and a handle 4.

The piercing tip 3 is located at one end of the obturator 2, and is formed in a piramidical shape. The handle 4 is located at the other end of the obturator 2 to pierce the piercing tip 3 into tissue.

The cannula 5 which forms a passage in the tissue punched by the piercing tip 3, thereby to insert an endoscope or a surgical tool into the body cavity, is formed from a flexible tube. The flexible tube is formed of polytetrafluoroethylene or polyurethane resin or polyvinyl chloride or other soft materials, and has a proximal open end and a distal open end to pass the piercing tip 3 of obturator 2.

A housing 6 mounted on the proximal open end of the cannula 5, is formed of polyurethane resin or other soft materials. The housing 6 is formed in a cylindrical shape, and has a rear open end to pass the piercing tip 3 of the obturator 2 therethrough.

A male screw 8 formed on the outer periphery of the housing 6, is screwed in a housing cap 7. The housing cap 7 which closes the rear open end of the housing 6, has an inlet nozzle 9 for inserting the obturator 2 into the cannula 5, and is provided with a seal ring 10 and a seal valve 11.

The seal ring 10 which seals airtightly the circumference of the obturator 2 inserted from the inlet nozzle 9, is installed at the end portion of the inlet nozzle 9. The seal ring 10 is formed of elastic materials, and has an inside diameter smaller than an outside diameter of the obturator 2.

The seal valve 11 which closes up the inlet nozzle 9 when the obturator 2 is pulled out from the cannula 5, is installed on the inside of the housing cap 7.

Figure 2:
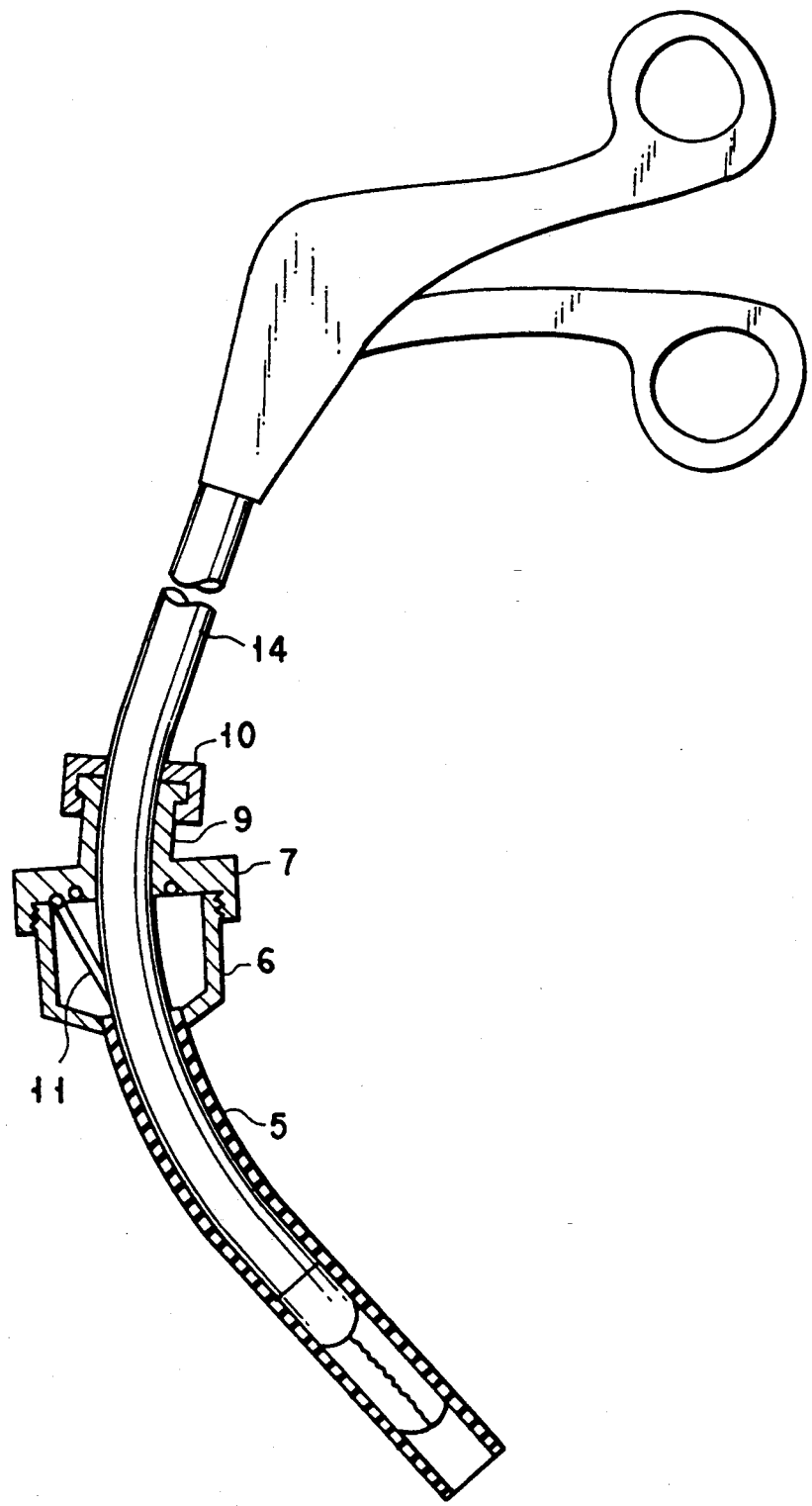
FIG. 2 is a sectional view schematically showing the cannula shown in FIG. 1.

In the trocar of this construction, as shown in FIG. 2, the cannula 5 transforms in accordance with the shape of surgical tools upon insertion of the surgical tool 14 curved in a circular arc into the cannula 5 from the inlet nozzle 9 after withdrawal of the obturator 2 from the cannula 5 inserted into the body cavity. Therefore, the trocar allows insertion of the surgical tool 14 curved in a circular arc into the body cavity through the cannula 5 without the necessity of enlarging the inside diameter of the cannula 5, and allows treatment of the bulla occurring at the back side of the lungs by the surgical tool 14.

Since the cannula 5 of the trocar transforms optionally in accordance with the shape of surgical tool, it allows insertion of not only surgical tools curved in a circular arc but also straight shaped surgical tools into the body cavity through the cannula 5.

Moreover, the trocar also transforms the housing 6 in accordance with the shape of the surgical tool 14. Therefore, it allows smoothly insertion of the surgical tool 14 curved in a circular arc into the cannula 5 with no necessity of enlarging the inside diameter of the inlet nozzle 9.

Figure 3A:
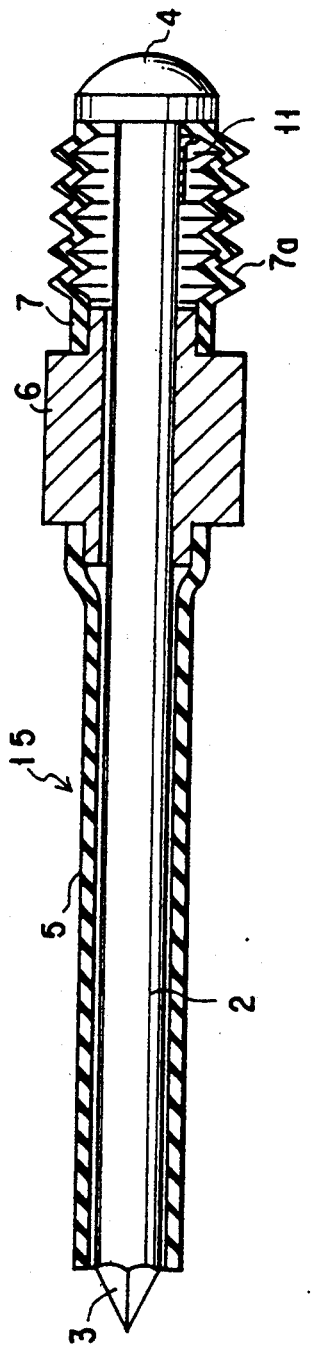
FIG. 3a is a sectional view of the trocar schematically showing a second embodiment of the invention.
Figure 3B:
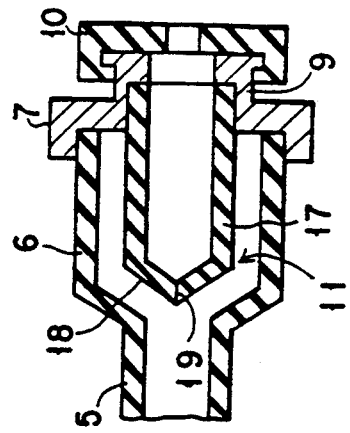

FIGS. 3a and 3b show a second embodiment of the trocar of the invention. The trocar 15 comprises an obturator 2 and a cannula 5. The obturator 2 is formed of stainless steel or other rigid materials, and has a piercing tip 3 for punching in a body cavity and a handle 4.

The piercing tip 3 is located at one end of the obturator 2, and is formed in a pyramidal shape. The handle 4 is located at other one end of the obturator 2 to pierce the piercing tip 3 into tissue.

The cannula 5 which forms a passage in the tissue punched by the piercing tip 3, thereby to insert an endoscope or a surgical tool into a body cavity, is formed from a flexible tube. The flexible tube is formed of polytetrafluoroethylene or polyurethane resin or polyvinyl chloride or other soft materials, and has a proximal open end and a distal open end to pass the piercing tip 3.

A housing 6 mounted on the proximal open end of the cannula 5, is formed of polyurethane resin or other soft materials. The housing 6 is formed in a thick cylindrical shape, and has a rear open end to passage the piercing tip 3 of the obturator 2. A housing cap 7 which closes the rear open end of the housing 6, is formed from a belows tube 12. The belows tube 12 is formed of soft materials, and has a rear end and a seal valve 11. The seal valve 11 which seals an open hole 7a formed at the rear end of the belows tube 12, is formed of elastic materials, and is installed at the inside of the housing cap 7.

In the trocar 15 of this construction, the cannula 5, the housing 6 and the housing cap 7 transforms in accordance with the shape of surgicals tool upon insertion of a surgical tool curved in a circular arc into the cannula 5 after extracting of the obturator 2 from the cannula 5. Therefore, the trocar 15, like the first embodiment described above, allows insertion of surgical tools curved in a circular arc into the body cavity through the cannula 5 without the necessity of enlarging the inside diameter of the cannula 5, and allows treatment of the bulla occurring at the back side of the lungs by the surgical tool inserted into the body cavity through the cannula 5.

Figure 4:
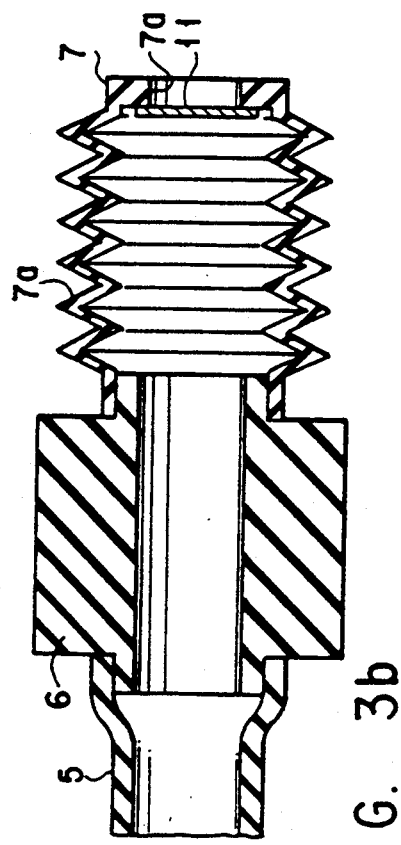
FIG. 4 is a sectional view of the trocar schematically showing a third embodiment of the invention.
Figure 5:
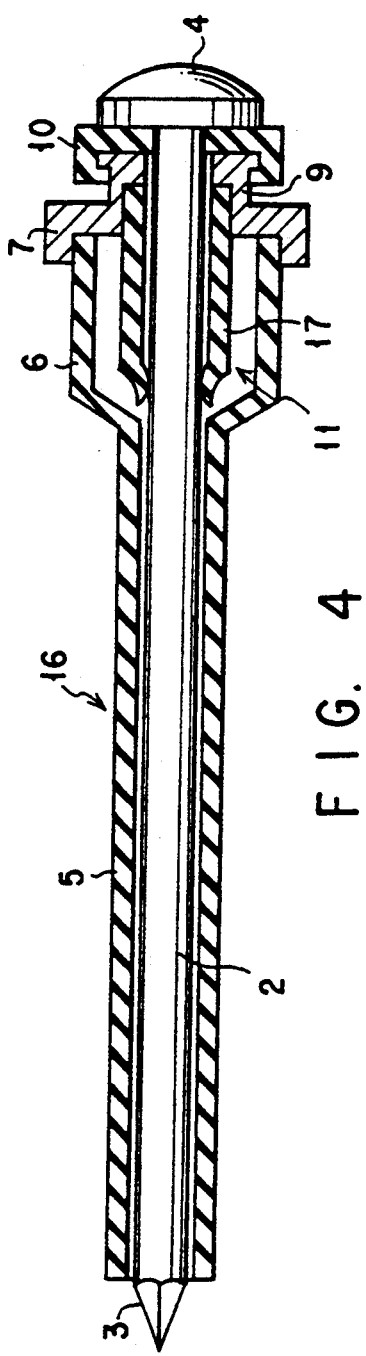
FIG. 5 is a sectional view of the housing shown in FIG. 4.

FIGS. 4 and 5 show a third embodiment of the invention. The trocar 16 comprises an obturator 2 and a cannula 5. The obturator 2 is formed of stainless steel or other rigid materials, and has a piercing tip 3 and a handle 4.

The piercing tip 3 is located at one end of the obturator 2, and is formed in a pyramidal shape. The handle 4 is located at other one end of the obturator 2 to pierce the piercing tip 3 into the tissue.

The cannula 5 which forms a passage in the tissue punched by the piercing tip 3 to insert an endoscope or a surgical tool into a body cavity, is formed from a flexible tube. The flexible tube is formed of polytetrafluoroethylene or polyurethane resin or polyvinyl chloride or other soft materials, and has a proximal open end and a distal open end to pass the piercing tip 3.

A housing 6 mounted on the proximal open end of the cannula 5, is formed of polyurethane resin or other soft materials. The housing 6 is formed in a cylindrical shape, and has a rear open end to passage the piercing tip 3 of the obturator 2.

A housing cap 7 which closes the rear open end of the housing 6, has an inlet nozzle 9 for inserting the obturator 2 into the cannula 5, and is provided with a seal ling 10 and a seal valve 11.

The seal ring 10 which seals airtightly the circumference of the obturator 2 inserted from the inlet nozzle 9, is installed at the end portion of the inlet nozzle 9. The seal ring 10 is formed of elastic materials, and has an inside diameter smaller than an outside diameter of the obturator 2.

The seal valve 11 which closes the inlet nozzle 9 when the obturator 2 is pulled out from the cannula 5, comprises an elastic tube 17 fixed to the inside of the inlet nozzle 9, a closing membrance 18 for closing one end of the elastic tube 17, and a slit 19 formed at the closing membrance 18.

In the third embodiment of the invention that has this construction, the cannula 5 and the housing 6 transforms in accordance with the shape of the surgical tool upon insertion of the surgical tool curved in a circular arc into the cannula 5 from the inlet nozzle 9 of the housing cap 7 after withdrawal of the obturator 2 from the cannula 5. Therefore, the third embodiment of the invention, like the above-mentioned the second embodiment, allows insertion of surgical tools curved in a circular arc into the body cavity through the cannula 5 without the necessity of enlarging the inside of the cannula 5, and allows treatment of the bulla occurring at the back side of the lungs with the surgical tool.

FIG. 6 shows a first modification example of the seal valve 11 shown in FIG. 4. The modification of the seal valve 11 features the formation of a seal 20 that usually is closed at the middle of the elastic tube 17.

FIG. 7 shows a second modification example of the seal valve 11 shown in FIG. 4. The modification of the seal valve 11 features the formation of a knot 21 at the middle of the elastic tube 17.

FIG. 8 shows a cannula assembly 22 of a fourth embodiment of the invention. The cannula assembly 22 comprises a cannula 5 and a seal device 23 mounted on one open end of the cannula 5. The cannula 5 is formed of polytetrafluoroethylene or other soft materials.

The seal device 23 has a ring plate 24a fixed to the cannula 5, a ring plate 24b located on the ring plate 24a, and a ring plate 24c located on the ring plate 24b. The ring plate 24a, 24b and 24c have path holes 25a, 25b, 25c at the center portion. The path hole 25a formed in the ring plate 24a has the largest inside diameter, and the path hole 25c formed in the ring plate 24c has the smallest inside diameter. The ring plate 24b and the ring plate 24c is rotatably supported around a support post 26 fixed to the ring plate 24a.

FIG. 9 shows the cannula assembly 22 with the ring plate 24b and 24c laid on top of the ring plate 24a. FIG. 10 shows the cannula assembly 22 with the ring plate 24b and 24c retreated from the ring plate 24a.

Therefore, the cannula assembly 22 of this construction may be insert surgical tools of relatively small diameter into the cannula 5 airtightly from the path holes 25a, 25b or 25c.

In the cannula assembly 22 of this construction, the cannula 5 transforms in accordance with the shape of the surgical tool upon insertion of the surgical tool curved in a circular arc. Therefore, the cannula assembly 22 allows insertion the surgical tool curved in a circular arc into the body cavity requiring no enlargement of the inside diameter of the cannula 5.

Figure 11:
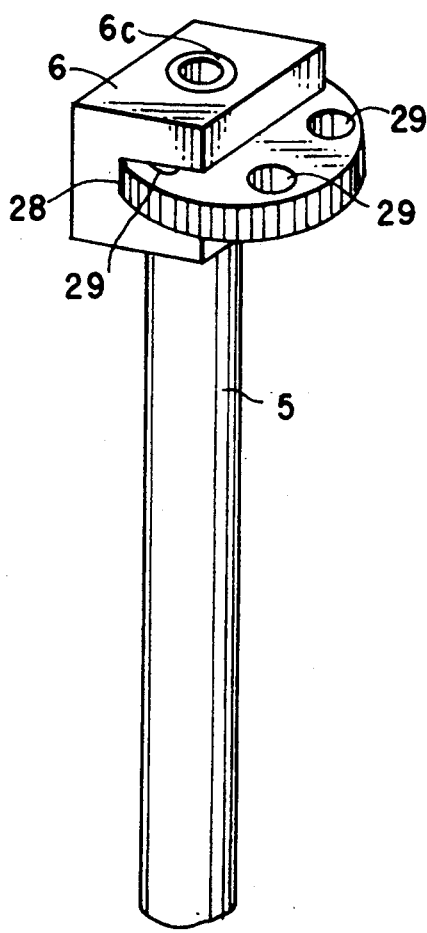
FIG. 11 is a external view showing a fifth embodiment of the invention.
Figure 12:
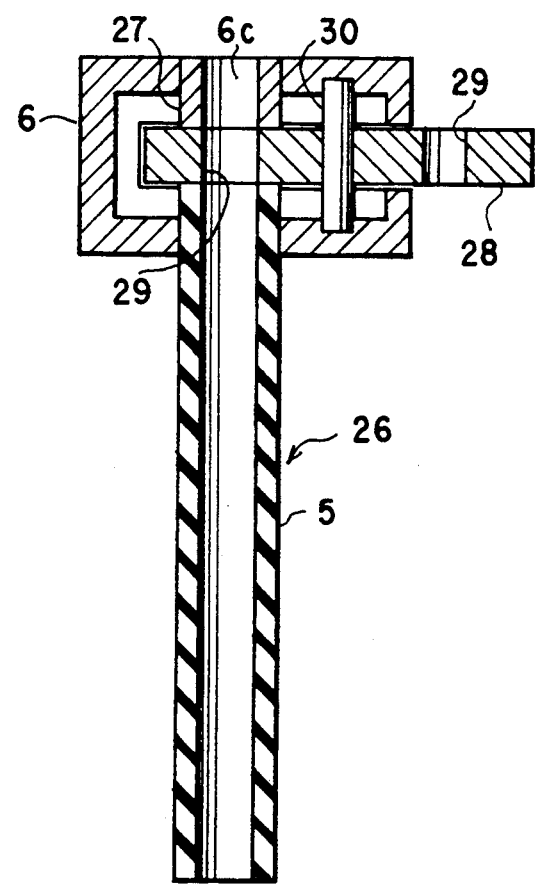
FIG. 12 is a sectional drawing of the cannula assembly shown in FIG. 11.

FIGS. 11 and 12 show a cannula assembly 26 of the trocar relating to a fifth embodiment of the invention. The cannula assembly 26 comprises a cannula 5 formed of polytetrafluoroethylene or other soft materials, and a housing 6 installed at one end of the cannula 5. The housing 6 is a box shaped and has a opening 6c for inserting the obturator or surgical tool into the cannula 5.

The cannula assembly 26 also comprises a guide tube 27 to guide the obturator or the surgical tool inserted from the opening 6c of the housing 6, and a rotating seal plate 28 for sealing airtightly the obturator or the surgical tool inserted into the cannula 5 through the guide tube 27. The rotating seal plate 28 is round shaped and has plural path holes 29 to pass airtightly the obturator or the surgical tool inserted from the opening 6c of the housing 6. These path holes 29 vary in diameter and are formed concyclically to the rotating seal plate 28.

The cannula assembly 26 also comprises a support axis 30 to support the rotation of the center part of the rotating seal plate 28 at a position eccentric from the center of the cannula 5.

The trocar assembly 26 of this construction allows airtight insertion of surgical tools of various diameters into the cannula 5. Moreover, the cannula 5 of the cannula assembly 26 transforms in accordance with the shape of surgical tools upon insertion of the surgical tool curved in a circular arc into the cannula 5. Therefore, the fifth embodiment of the invention, like the above-mentioned the fourth embodiment, allows insertion of the surgical tool curved in a circular arc into the body cavity through the cannula 5 requiring no enlargement of the inside diameter of the cannula 5.

Figure 13:
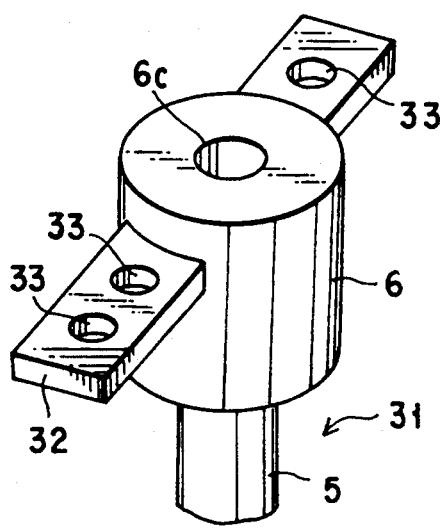
FIG. 13 is a external view showing a sixth embodiment of the invention.
Figure 14:
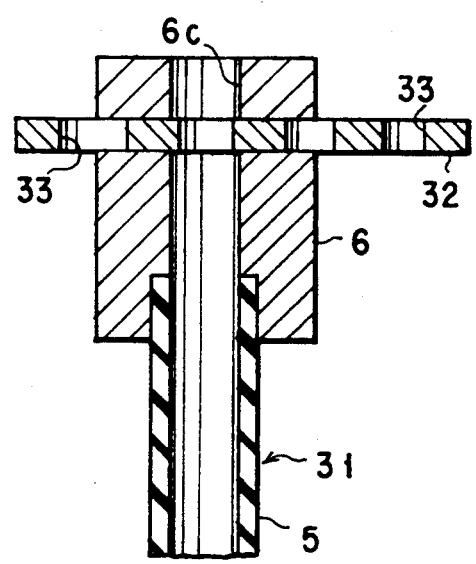
FIG. 14 is a sectional drawing of the cannula assembly shown in FIG. 13.

FIGS. 13 and 14 show a sixth embodiment of the invention. The cannula assembly 31 comprises a cannula 5 formed of polytetrafluoroethylene or other soft materials, and a housing 6 installed at one end of the cannula 5. The housing 6 is cylinder shaped and has an open hole 6c for insertion of the obturator or surgical tool into the cannula 5.

The cannula assembly 31 also comprises a slide seal plate 32 for airtight sealing of the circumference of the obturator or the surgical tool inserted from the open hole 6c of the housing 6. The slide seal plate 32 is slidable installed so that it crosses the open hole 6c of the housing 6, and has plural path holes 33 of different diameters. These path holes 33 are formed along the slide direction of the slide seal plate 32.

Therefore, the cannula assembly 31 of this construction allows airtight insertion of various surgical tools of different diameters into the cannula 5 Moreover, the cannula 5 of the cannula assembly 31 transforms in accordance with the shape of surgical tools upon insertion of the surgical tool curved in a circular arc into the cannula 5. Therefore, it allows insertion of the surgical tool curved in a circular arc into the body cavity through the cannula 5 requiring no enlargement of the inside diameter of the cannula 5.

FIGS. 15 and 16 show a cannula assembly 35 of the trocar relating to the seventh embodiment of the invention. The cannula assembly 35 comprises a cannula 5 formed of polytetrafluoroethylene or other soft materials, and a housing 6 installed at one end of the cannula 5. The housing 6 is formed in a box shape and has an opening 6c to insert the obturator or the surgical tool into the cannula 5. A first seal cap 36 encased in the opening 6c has a path hole 37 to pass the obturator or the surgical tool airtightly.

A second seal cap 38 installed on the side face of the housing 6, has an outside diameter for encasement in attachable and detachable way to the path hole 37 of the seal cap 36. The seal cap 38 has a path hole 39 smaller in diameter than the path hole 37 of the seal cap 36. The path hole 39 of the seal cap 38 encases in a freely attachable and detachable way to a convex 40 installed at the side face of the housing 6.

The cannula assembly 35 of this construction allows airtight insertion of small diameter surgical tools into the cannula 5 since the encasement of the seal cap 38 to the seal cap 36 reduces the size of the opening formed in the housing 6.

The cannula 5 of the cannula assembly 35 transforms in accordance with the shape of surgical tools upon insertion of the surgical tool curved in a circular arc into the cannula 5. Therefore, the seventh embodiment of the invention allows insertion of the surgical tool curved in a circular arc into the body cavity through the cannula 5 not requiring enlargement of the inside diameter of the cannula 5.

FIGS. 17 and 18 show a modification example of the cannula assembly shown FIG. 15. The cannula assembly of the modification examples is arranged so that the size of the opening of the housing 6 is changed by the second seal cap 38 and a third seal cap 41 installed at the side of housing 6.

FIGS. 19 and 20 show a cannula assembly of the trocar relating to an eighth embodiment of the invention. The cannula assembly comprises a cannula 5 and a housing 6. The cannula 5 is formed of soft materials, and has a proximal open end and a distal open end. The housing 6 mounted on the proximal open end of the cannula 5, is formed of elastic materials, and has a rear end surface and an opening 6c formed in the rear end surface.

An elastic seal 40 formed in a unit with the housing 6, is formed in a tent shape, and has opposing two slants 41a and 41b.

Path holes 42a and 42b formed in the slants 41a and 41b of the elastic seal 40, have different inside diameters, and are closed by elastic closing membranes 43a and 43b with slits.

The cannula assembly of this construction seals the opening 6c of the housing 6 airtightly since the slant 41a of the elastic seal 40 contacts closely the rear end surface of the housing 6 as shown in FIG. 21 upon insertion of a relatively large diameter surgical tool 14 from the path hole 42a formed on the slant 41a of the elastic seal 40.

Moreover, the eight embodiment of the invention transforms the cannula 5 in accordance with the shape of surgical tools upon insertion of the surgical tool curved in a circular arc into the cannula 5. Therefore, the eight embodiment of the invention allows insertion of the surgical tool curved in a circular arc into the body cavity through the cannula 5 not requiring the enlargement of the inside diameter of the cannula 5.

Figure 22A:
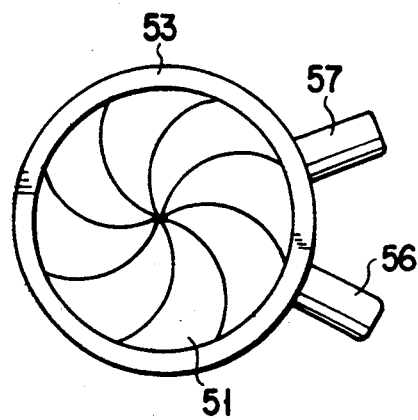
FIGS. 22a, 22b, 23a and 23b are drawings of the trocar showing a ninth embodiment of the invention.
Figure 22B:
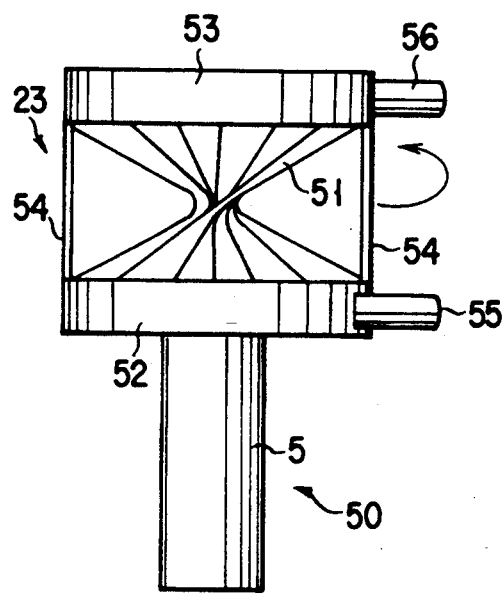

FIG. 22a and 22b show a cannula assembly of the trocar relating to a ninth embodiment of the invention. The cannula assembly 50 comprises a cannula 5 and a seal device 23. The cannula 5 is formed of soft materials, and has a proximal open end and a distal open end.

The seal device 23 comprises a circular ring flame 52 fixed on the proximal open end of the cannula 5, an elastic thin tube 51 having one end fixed to the circular ring flame 52, and a circular ring flame 53 fixed on other one end of the elastic thin tube 51. The elastic thin tube 51 is given twisting force by plural rubber strings 54 installed between the circular ring flame 52 and 53. The circular ring flame 52 and 53 have finger hooks 55 and 56 to rotate the circular ring flame 53 against the twisting force given by the rubber strings 54.

Figure 23A:
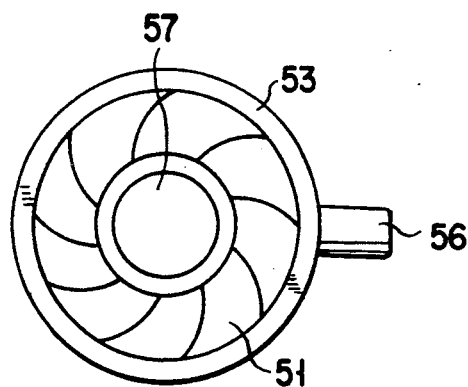
Figure 23B:
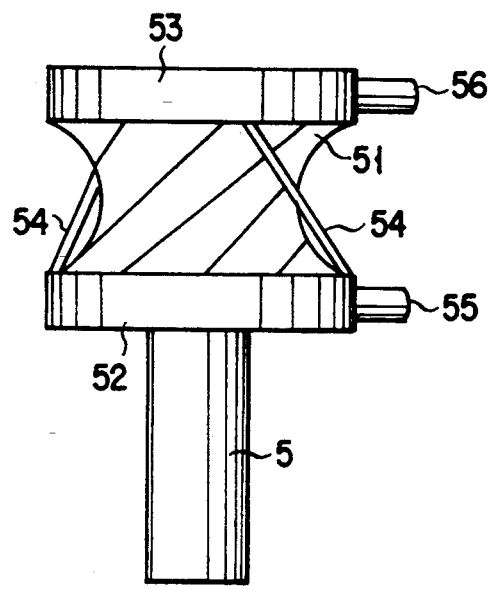

Therefore, the cannula assembly 50 of this construction allows airtight insertion of various surgical tools of different diameters into the cannula 5 since an insertion passage 57 is formed at the center of the elastic thin tube 51 as shown in FIG. 23a and 23b when the circular ring flame 53 is set to rotation against the force given by the rubber strings 54.

FIGS. 24a and 24b show a cannula assembly 58 of the trocar relating to a tenth embodiment of the invention. The cannula assembly 58 comprises a cannula 5 and a housing 6 fixed to one end of the cannula 5. The housing 6 has an opening 6c for inserting the obturator or the surgical tool 14 into the cannula 5, and a seal device 23 for closing airtightly the opening 6c.

The seal device 23 comprises a cylinder 59 installed at the inside of the housing 6, and a seal ring 60 inserted in the cylinder 59. The seal ring 60 is formed of elastic materials, and has an inner circumferences closed in the natural state.

Therefore, the cannula assembly 58 of this construction may be seal the circumferences of the surgical tool 14 airtightly by the seal ring 60.

FIGS. 25a and 25b show a cannula assembly 63 of the trocar relating to an eleventh embodiment of the invention. The cannula assembly 63 comprises a cannula 5 and a housing 6 fixed to one end of the cannula 5. The housing 6 has an opening 6c for inserting the obturator or the surgical tool 14 into the cannula 5, and a seal device 23 for closing airtightly the opening 6c.

The seal device 23 comprises a ring balloon 65 accommodated in the housing 6, a belows tube 67 jointed to the ring balloon 65, and a operation member 66 installed at one end of the belows tube 67. The operation member 66 has a convex 68 that block nails 69 formed on the housing 6.

The cannula assembly 63 of this construction may be seal airtightly the circumferences of the surgical tool or the obturator inserted from the opening 6c of the housing 6 by the balloon 65.

FIG. 26 shows a cannula assembly 70 of the trocar relating to a twelfth embodiment of the invention. The cannula assembly 70 comprises a soft cannula 5 and a housing 6 fixed to one end of the soft cannula 5. The housing 6 is formed from an elastic tube. The rear end of the housing 6 is drawn inside and forms a seal 71.

FIG. 27 shows a cannula assembly 72 of the trocar relating to a thirteenth embodiment of the invention. The cannula assembly 72 comprises a cannula 5, a flange 73 formed at one end of the cannula 5, a seal ring 74 set rotatably on the flange 73, and a seal ring 75 set rotatably on the seal ring 74.

The seal ring 74 and 75 have frames 76 formed in a ring shape, seal membranes 77 kept in a stretched state on the frame 76, and slits 78 formed at the central portion of the seal membrance 77.

FIG. 28 shows a cannula assembly 80 of the trocar relating to a fourteenth embodiment of the invention. The cannula assembly 80 comprises a cannula 5 and a housing 6. The cannula 5 is formed of soft materials, and has a proximal open end and a distal open end.

The housing 6 is mounted on the proximal open end of the cannula 5, and has rear open end. A housing cap 7 which closes the rear open end of the housing 6, has an inlet nozzle 9 to insert the obturator into the cannula 5. The housing cap 7 is provided with a seal cap 81 and a seal valve 11.

The seal cap 81 which seals airtightly the circumference of the obturator inserted from the inlet nozzle 9, is installed at the end portion of the inlet nozzle 9, and has a slit 81a. The slit 81a is formed at the central portion of the seal cap 81.

The seal valve 11 which maintains the airtightness of the body cavity, comprises an elastic tube 84 fixed to the inlet nozzle 9, and a valve seat 83 installed at one open end of the elastic tube 84 via a supporting member 84a. The supporting member 84a has elasticity. The one open end of the elastic tube 84 is closed by the valve seat 83 supported the supporting member 84a.

In the fourteenth embodiment of the invention, the cannula 5 transforms in accordance with the shape of surgical tool upon insertion of a surgical tool curved in a circular arc through the inlet nozzle 9 of the housing cap 7. Therefore, the trocar allows insertion of a surgical tool curved in a circular arc into the body cavity through the cannula 5 requiring no enlargement of the inside diameter of the cannula 5.

Moreover, the trocar disclose the elastic tube 84 in accordance with the shape of surgical tool upon insertion of the surgical tool curved in a circular arc through the inlet nozzle 9 of the housing cap 7. Therefore, it allows smooth insertion of the surgical tool curved in a circular arc into the cannula 5 with no necessity of enlarging the inside diameter of the inlet nozzle 9.

FIG. 29 shows a cannula assembly 85 of the trocar relating to a fifteenth embodiment of the invention. The cannula assembly 85 comprises a cannula 5 and a housing 6. The cannula 5 is formed of soft materials, and has a proximal open end and a distal open end.

The housing 6 is mounted on the proximal open end of the cannula 5, and has rear open end. A housing cap 7 which closes the rear open end of the housing 6, has an inlet nozzle 9 to insert the obturator into the cannula 5. The housing cap 7 is provided with a seal cap 81 and a seal valve 11.

The seal cap 81 which seals airtightly the circumference of the obturator inserted from the inlet nozzle 9, is installed at the end portion of the inlet nozzle 9, and has a slit 81a. The slit 81a is formed in the central portion of the seal cap 81.

The seal valve 11 which maintains the airtightness of the body cavity, comprises an elastic plate 86 fixed to the inner surface of the housing 6, a valve 83 for closing an open 86a formed at the central portion of the elastic plate 86, and a supporting member 84a for supporting the valve 83. The supporting member 84a is fixed to the elastic plate 86.

The cannula assembly 80 of this construction dislocates the elastic plate 86 in accordance with the shape of surgical tools when a surgical tool curved in a circular arc is inserted into the cannula 5 through the opening 86a of the elastic plate 86. Therefore, the cannula assembly 80 allows smooth insertion of surgical tools curved in a circular arc into the cannula 5 requiring no enlargement of the inside diameter of the inlet nozzle 10.

Figure 30:
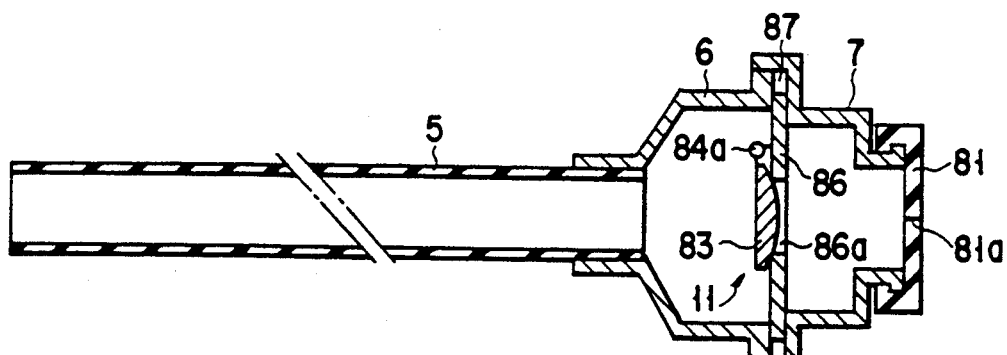
FIG. 30 is a sectional view showing a sixteenth embodiment of the invention.

FIG. 30 shows a cannula assembly of the trocar relating to a sixteenth embodiment of the invention. The cannula assembly comprises a cannula 5 and a housing 6. The cannula 5 is formed of soft materials, and has a proximal open end and a distal open end.

The housing 6 is mounted on the proximal open end of the cannula 5, and has rear open end. A housing cap 7 which closes the rear open end of the housing 6, has an inlet nozzle 9 to insert the obturator into the cannula 5. The housing cap 7 is provided with a seal cap 81 and a seal valve 11.

The seal cap 81 which seals airtightly the circumference of the obturator inserted from the inlet nozzle 9, is installed at the end portion of the inlet nozzle 9, and has a slit 81a. The slit 81a is formed in the central portion of the seal cap 81.

The seal valve 11 which maintains the airtightness of the body cavity, comprises a support plate 86, a valve 83 for closing an open 86a formed at the central portion of the support plate 86, and a supporting member 84a for supporting the valve 83. The supporting member 84a is fixed on the support plate 86. The support plate 86 is encased slidably in a ring groove 87 formed at the inner surface of the housing 6.

Cannula assembly of this construction dislocates the support plate 86 in accordance with the shape of surgical tools when a surgical tool curved in a circular arc is inserted into the cannula 5 from the inlet nozzle 9 through the opening 86a of the support plate 86. Therefore, the cannula assembly allows smooth insertion of the surgical tool curved in a circular arc into the cannula 5 requiring no enlargement of the inside diameter of the inlet nozzle 9.

Figure 31A:
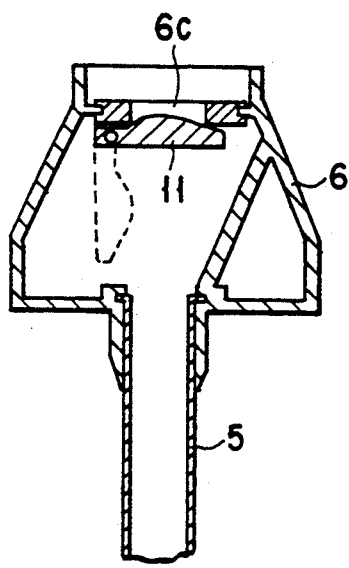
FIGS. 31a and 31b are sectional views showing modification examples of the seal valve shown in FIG. 30.
Figure 31B:
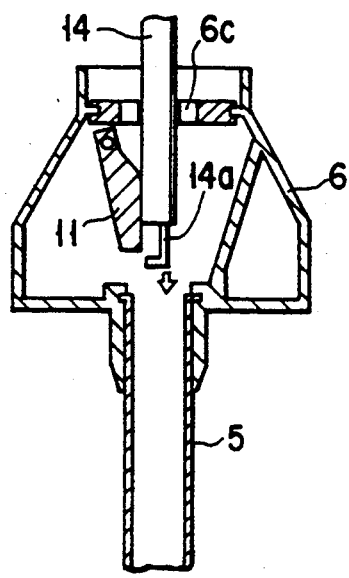

FIGS. 31a and 31b show modified examples of the seal valve 11. The front end of the seal valve 11 is formed in a smooth curved surface to prevent a hook 14a of the surgical tool 14 from being caught in the seal valve 11 upon withdrawal of the surgical tool 14 with the hook 14a at the front end of the seal valve 11 from the cannula 5.

Figure 32:
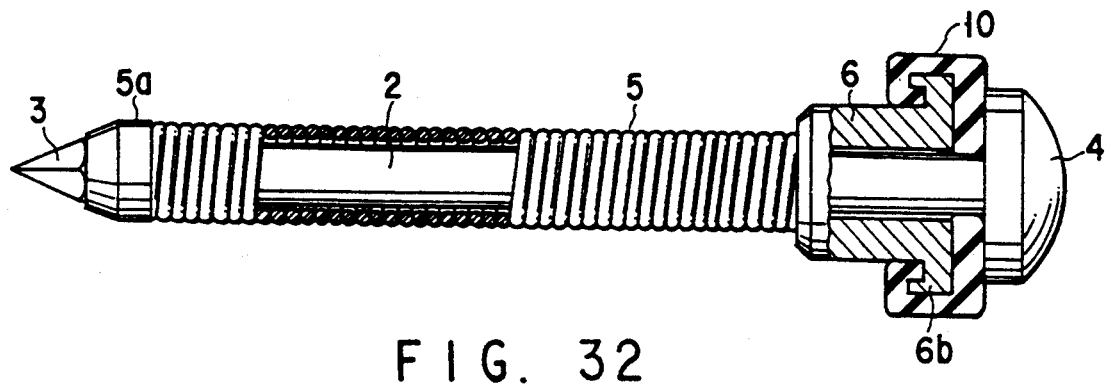
FIGS. 32 and 33 are drawings showing a seventeenth embodiment of the invention.

FIG. 32 shows the trocar of a seventeenth embodiment of the invention. The trocar comprises an obturator 2 and a cannula 5. The obturator 2 is formed of stainless steel or other rigid materials, and has a piercing tip 3 and a handle 4.

The piercing tip 3 which pinks in tissue, is located at one end of the obturator 2, and is formed in a piramidcal shape. The handle 4 is located at other one end of the obturator 2 to pierce the piercing tip 3 into the tissue.

Figure 33:
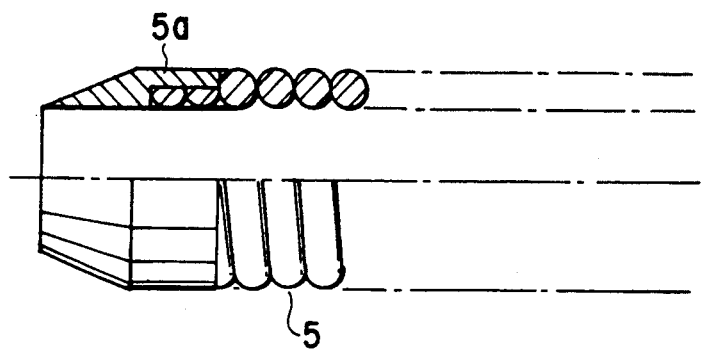

The cannula 5 which forms a passage in the tissue punched by the piercing tip 3 to insert an endoscope or a surgical tool into a body cavity, is formed from a coil tube. The coil tube is formed with a wire formed of stainless steel or other materials, and has a proximal open end and a distal open end to pass the piercing tip 3 of obturator 2. A front end ring 5a fixed to the distal open end of the cannula 5, as shown in FIG. 33, has its front end portion formed narrow to decrease the resistance to tissue.

A housing 6 mounted on the proximal open end of the cannula 5, has a rear open end to passage the piercing tip 3 of the obturator 2. A seal ling 10 installed at the rear open end of the housing 6, is formed of elastic materials to seal airtightly the circumference of the obturator 2 inserted from the rear open end of the housing 6.

In the trocar of this construction, the cannula 5 transforms in accordance with the shape of surgical tools upon insertion of a surgical tool curved in a circular arc into the cannula 5 from the rear open end of the housing 6. Therefore, the trocar allows insertion of the surgical tool curved in a circular arc into the body cavity through the cannula 5 requiring no enlargement of the inside diameter of the cannula 5. Further, since the cannula 5 is formed of a coil tube, even when it is pushed against the tissue, it is not deformed in the axial direction thereof. In other words, the strength of the cannula 5 formed of a coil tube is higher than that of a cannula that is formed of a soft material.

Figure 34:
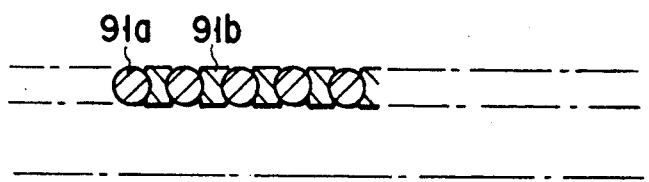
FIGS. 34, 35, 36 and 37 are drawings showing modification examples of the cannula shown in FIG. 32.

FIGS. 34, 35, 36 and 37 show modified examples of the cannula 5 shown in FIG. 32. The cannula 5 shown in FIG. 34, is formed from a coil tube having two wire 91a and 91b. The wire 91a has its section formed in a circle shape. The wire 91b has its section formed in a rectangle shape.

Figure 35:
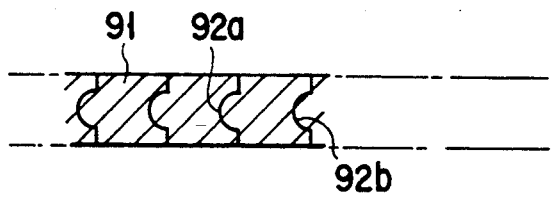

In the modified example shown in FIG. 35, the section of a wire 91 forming the coil tube is formed in a rectangle shape. The sides of the wire 91 are formed with a convex spiral 92a and a groove 92b encasing into convex spiral formed in the lengthwise direction from the wire 91.

Figure 36:
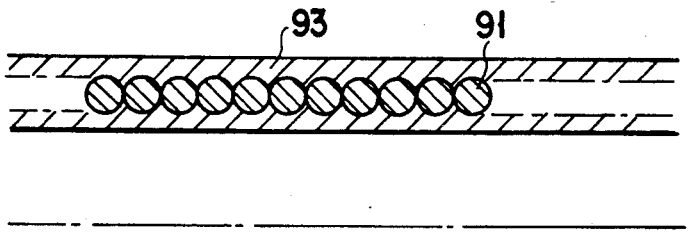

The modified example shown in FIG. 36, has a waterproof resin layer 93 formed on the periphery and inner perimeter of the coil tube forming the cannula 5.

Figure 37:
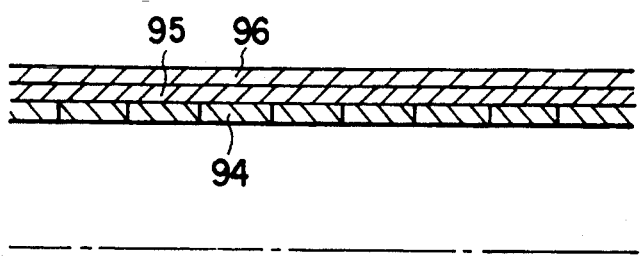

The modified example shown in FIG. 37, has the cannula 5 formed with a spiral tube 94, with the periphery of spiral tube 94 coated with a net tube 97 and the periphery of net tube 97 coated with a soft tube 96.

FIGS. 38 and 39 shows the trocar of an eighteenth embodiment of the invention. The trocar comprises an obturator 2 and a cannula 5. The obturator 2 is formed of stainless steel or other rigid materials, and has a piercing tip 3 and a handle 4.

The piercing tip 3 which pinks in tissue, is located at one end of the obturator 2, and is formed a piramidcal shape. The handle 4 is located at other one end of the obturator 2 to pierce the piercing tip 3 into the tissue.

The cannula 5 which forms a passage in the tissue punched by the piercing tip 3 to insert an endoscope or a surgical tool into a body cavity, is formed from a flexible tube having a cannula flange 5b. The cannula flange 5b is formed at a rear end of the cannula 5.

A protecting sleeve 99 located at the periphery of the cannula 5, is formed of stainless steel or other hard material, and freely slides in the lengthwise direction of the cannula 5. The sleeve 99 has a flange 99a at a rear end of it.

The stopper sleeve 100 located at the rear end of the sleeve 99 is formed of stainless steel or other hard materials in a semicircular shape.

The trocar of this construction, as shown in FIGS. 40a, 40b, 40c, has the front end of the cannula 5 project from the front end of the protecting sleeve 99 when the flunge 5b formed in the rear end of the cannula 5 contacts the sleeve 99 after removal of the stopper sleeve 100 from the cannula 5 inserted into tissue 101. Therefore, the eighteenth embodiment of the invention prevent compression of the cannula 5 when the piercing tip 3 of the obturator 2 is pierced into the body cavity, and allows smooth insertion of the cannula 5 into the body cavity without deformation under compression of the front end of the cannula 5.

Figure 41:
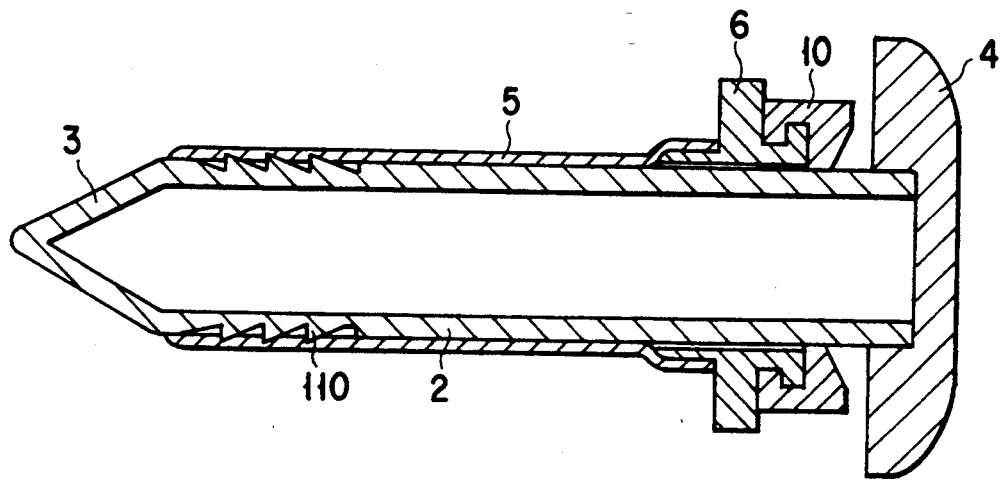
FIGS. 41 and 42 are drawing showing a nineteenth embodiment of the invention.

FIG. 41 shows the trocar of a nineteenth embodiment of the invention. The trocar includes an obturator 2 and a cannula 5. The obturator 2 is formed with stainless steel or other rigid materials, and has a piercing tip 3 and a handle 4.

The piercing tip 3 for pinking in a body cavity, is located at one end of the obturator 2, and is formed in a pyramidal shape. The handle 4 is located at other one end of the obturator 2 to pierce the piercing tip 3 into tissue.

The cannula 5 which forms a passage in the tissue punched by the piercing tip 3 to insert an endoscope or a surgical tool into the body cavity, is formed from a flexible tube. The flexible tube is formed of polytetrafluoroethylene or polyurethane resin or polyvinyl chloride or other soft materials, and has a proximal open end and a distal open end to pass the piercing tip 3.

A housing 6 mounted on the proximal open end of the cannula 5, has a rear open end to passage the piercing tip 3 of the obturator 2.

A seal ling 10 which seals airtightly the circumference of the obturator 2 inserted from the rear open end of the housing 6, is formed of elastic materials, and has an inside diameter smaller than an outside diameter of the obturator 2.

The obturator 2 has blocking nails 110 to prevent compression of the cannula 5 when the piercing tip 3 is pierced into the body cavity. The blocking nails 110 formed at the front end portion of the obturator 2 locks with the inner perimeter of the cannula 5.

The trocar of this construction has blocking nails 110 caught into the inner perimeter of the cannula 5 when the piercing tip 3 is pierced into the body cavity, and prevent the compression of the cannula 5 by blocking nails 110.

The trocar of this construction prevent infections as blocking nails 110 is caught on the inner perimeter of the cannula 5 when insertion of the obturator 2 from the rear end opening of the cannula 5 is attempted, and the obturator 2 withdrawn from the cannula 5 is not reused.

Figure 42:
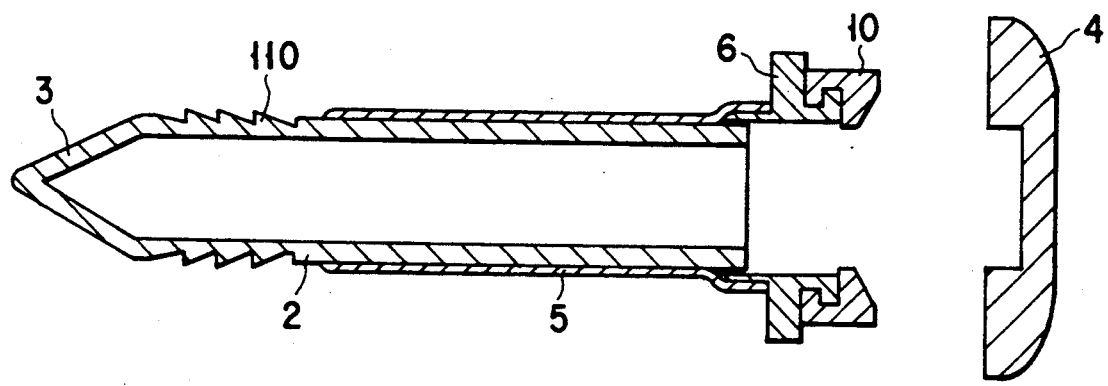

Since the trocar has blocking nails 110 installed on the front end periphery of the obturator 2, the obturator 2 can not be inserted from the rear end side of the cannula 5. Therefore, when installing of the handle 4 at the base end of the obturator 2, the handle 4 may be installed at the base end of the obturator 2 after insertion of the obturator 2 from the front end side of the cannula 5 as shown in FIG. 42.

A twentieth embodiment of the invention is explained with FIGS. 43, 44, 45, 46 and 47 as a reference.

Figure 44:
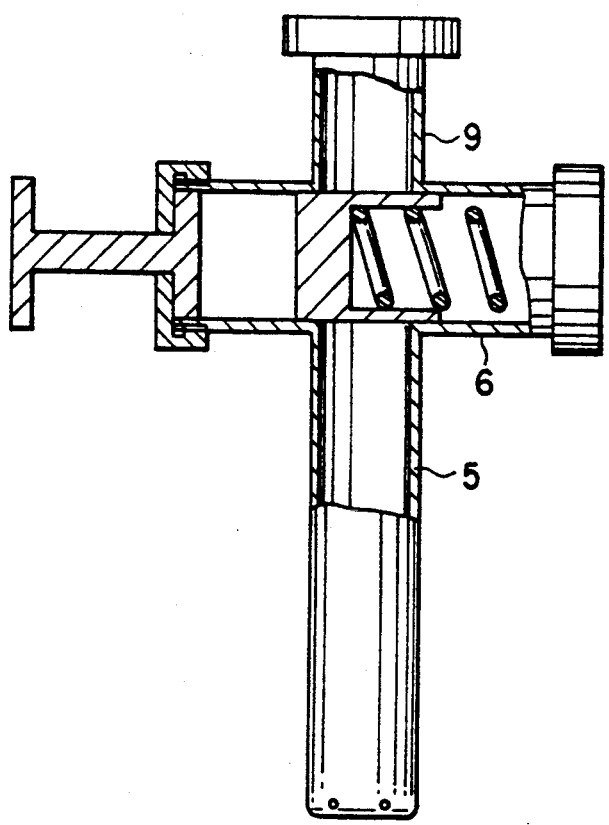
FIG. 44 is a side view showing the cannula shown in FIG. 43.
Figure 45:
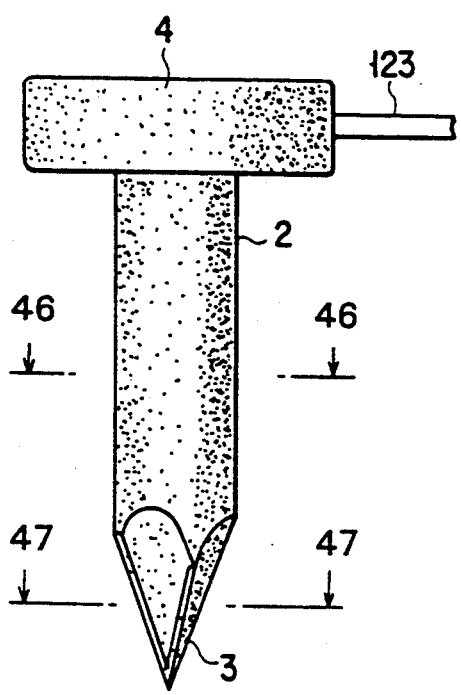
FIG. 45 is a side view of the obturator shown in FIG. 43.
Figure 46:
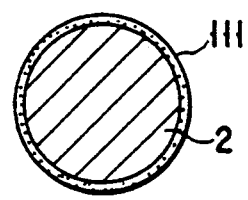
FIG. 46 is a sectional view taken on line A—A of FIG. 45.
Figure 47:
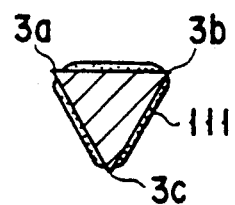
FIG. 47 is a sectional view taken on line B—B of FIG. 45.

An obturator 2 is formed of stainless steel or other conductive materials, and has a piercing tip 3 and a handle 4. The piercing tip 3 is formed in a pyramidal shape, and has three cut edges 3a, 3b and 3c, as shown FIG. 47. Fluoric resin insulator coating 111 is applied to the whole surface of the obturator 2 to mask the cut edges 3a, 3b and 3c of the piercing tip 3. With the exception of the cut edges 3a, 3b and 3c of the piercing tip 3, the surface of the obturator 2 is insulated by the insulation coating 111. FIG. 44 shows the condition of the insulation coating 111 as a section along A—A line, and FIG. 45 shows it as a section along B—B line. The materials of insulation coating 111 may be any insulation materials such as ceramics and silicone resins.

The output of a high frequency generating circuit 120 for generating high frequency voltage is supplied to a primary coil of a transformer 122 through a power control circuit 121. The power control circuit 121 controls the current circulation from the high frequency generating circuit 120 to the transformer 122 and responds to an output of a breaking circuit 128.

The base end of the obturator 2 is connected electrically via a cable 123 to one end of a secondary coil of the transformer 152. A patient plate 124 for installation on the skin of the patient is connected electrically via a cable 125 to the other end of the secondary coil of the transformer 122. In other words, it is so arranged that the high frequency voltage generated at the secondary coil of the transformer 122 is impressed between the cut edges 3a, 3b and 3c of the piercing tip 3 and the patient plate 154.

A current detector 126 is installed on the current circulation route from one end of the secondary coil of the transformer 122 to the cable 123. The current detector 126 detects the current flowing to the secondary coil of the transformer 122, and the detection results are sent to a CPU 127.

The CPU 127 compares the detection results of the current detector 126 with values fixed in advance, and sends out current circulation stoppage order if the detection results get lower than the fixed values. The current circulation stoppage order is sent to the breaking circuit 128 and an alarm circuit 129.

The breaking circuit 128 responds to the current circulation stoppage order from the CPU 127 and breaks the current circulation of the power control circuit 121. The alarm circuit 128 responds to the current circulation stoppage order from the CPU 127 and sends out visional or auditory alarm of light or sound.

Therefore, when the high frequency generating circuit 120 acts, the high frequency voltage is impressed between the obturator 2 and the patient plate 124.

When the cut edges 3a, 3b and 3c of the piercing tip 3 exposed from the insulation coating 121 contact tissue, a closed circuit is formed at the secondary coil side of the transformer 122 through the body, and the high frequency current flows at high density to the puncture site of the body cavity. This burns off the puncture site.

Therefore, even if the cut edges 3a, 3b and 3c of the piercing tip 3 are worn out, sufficient sharpness is secured and constantly stable incision force can be obtained.

When the piercing tip 3 of the obturator 2 penetrates the tissue and pierces in the body cavity, the resistance between the obturator 2 and the patient plate 124 gets larger and the current flowing at the secondary coil side of the transformer 122 decreases. The current detector 126 and the CPU 127 detect the decrease in the secondary side current, and the breaking circuit 128 and the alarm circuit 129 responds to the detection. In other words, alarm is sent out upon breakage of high frequency current.

Therefore, even if the piercing tip 3 of the obturator 2 contacts an organ in the body cavity, the high frequency current never flows to the organ. Additionally, since the alarm is sent out, the operator can swiftly notice that piercing tip 3 of the obturator 2 is reached the body cavity, and safety improves. Reinsertion can be performed by means of resetting procedures described in the manual for the operators.

Though the embodiment is limited to current circulation introduction or breaking at the power control circuit 121, construction may be added so that the CPU 127 detects sequentially the thickness of puncture balance at the body in accordance with the current value detected by the current detector 126 and the current circulation volume at the power control circuit 121 is adjusted in accordance with the detected thickness. In this case, the effect on the body may be minimized since the high frequency current decreases in proportion to the decrease in the thickness of puncture balance.

Figure 48:
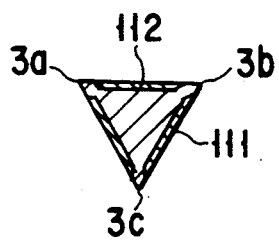
FIG. 48 is a drawing showing a first modification of the obturator shown in FIG. 46.

FIG. 48 shows a first modification example of the obturator 2 shown in FIG. 45. The modification example has hollows 112 at each face of the piercing tip 3 of the obturator 2. The insulation coating 111 for insulating the surface of the obturator 2, is formed at the hollows 112 like not to project from the each face of the piercing tip 3, thereby to touch certainly the cut edges 3a, 3b and 3c of the obturator 2 to the tissue.

Figure 49:
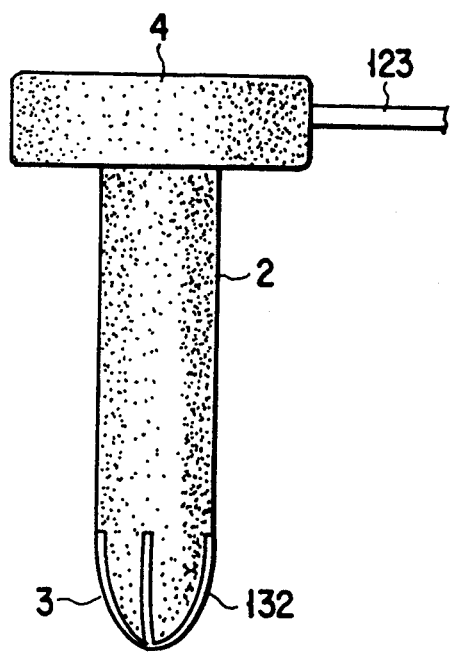
FIGS. 49, 50 and 51 are drawings showing a second modification example of the obturator shown in FIG. 46.
Figure 50:
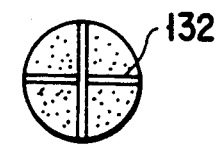
Figure 51:
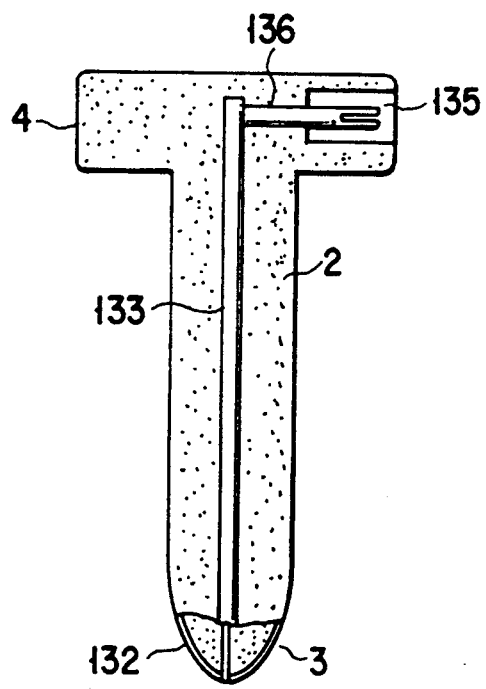
Figure 56:
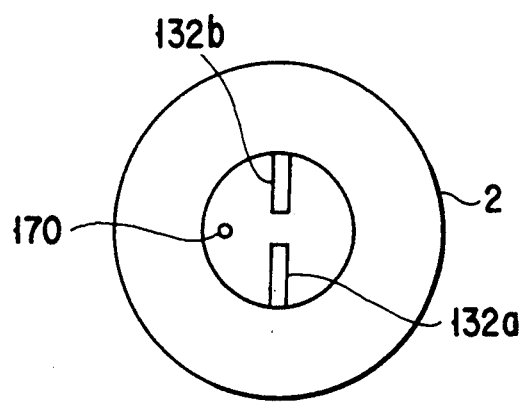

FIGS. 49, 50 and 51 show a second modification example of the obturator 2 shown in FIG. 45. The modifications example has an obturator body 130 formed of insulation materials. The obturator body 130 formed in a rod shape, and has a piercing tip 3 at one end. The piercing tip 3 is formed in a spherical cone, and has an electrode 132 formed in a cross shape.

The electrode 132 is formed at one end of a conductive rod 133 located at the axis core of the obturator body 130. The conductive rod 133 has a pin plug 136 for connection of the cable 123 at other end.

FIG. 52 shows a third modification example of the obturator 2 shown in FIG. 45.

The obturator 2 shown in FIG. 52 has a tapering (corresponding to piercing tip 3) 131 with a triangle section at the front end of a rod-shaped obturator body 130 formed of insulation materials such as ceramics and plastics. An electrode 132 is installed in embedded condition along the ridgeline of each edge of the tapering 131.

The electrode 132 is formed, as shown in FIG. 53, in an anchor shape in a unit in practically at the front end of a conductive axis rod 133 located at the axis core of the obturator body 130. On the other hand, an insertion passage 134a is formed in the axis core of the obturator body 130, and the electrode 132 is installed by means of insertion of the axis rod 133 from the front end side into the insertion passage 134a.

A concave 135 for connection of the cable 123 is formed at the base end of the obturator body 130, and an insertion passage 134b is formed from the inner bottom surface of the connective concave 135 in the condition of crossing directly insertion the passage 134a. A pin plug 136 is inserted into the connective concave 135 and the insertion passage 134b. The pin plug 136, as shown in FIG. 54, has slits 137a and 137b at front and base ends. The slits 137a and 137b are formed along the axis direction of the pin plug 136. The cable 123 is connected to the slit 137b of the pin plug 136.

The axis rod 133 has a narrow diameter part 133a at the location corresponding to the insertion passage 134a so that the slit 137a of the pin plug 136 grips the narrows diameter part 133 of the axis rod 133 when the pin plug 136 is inserted into the insertion passage 134a. The pin plug 136 is linked to the axis rod 133, and the cable 123 and the electrode 132 get in current circulation condition.

Figure 57:
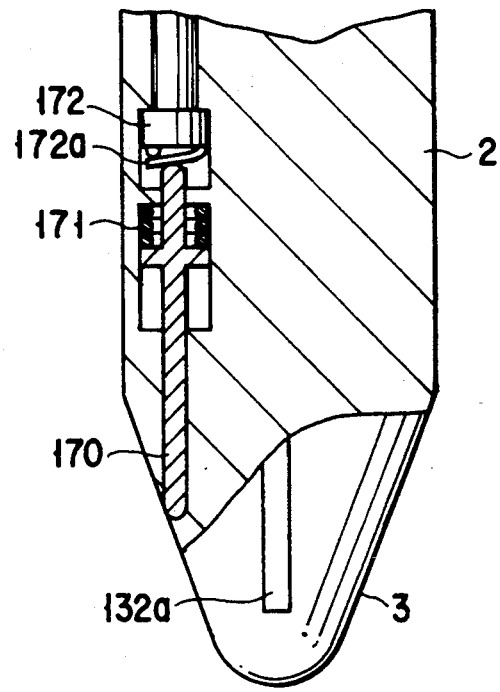

FIG. 55 shows a modification example shown FIG. 43. The trocar of the example has a detection rod 170 at the front end of the obturator 2. The detection rod 170, as shown in FIG. 57, advances and retreats freely in the axis direction of the obturator 2, and is given force in the direction of the front end of the obturator 2 by a spring 171 incorporated in the obturator 2. The base end of the detection rod 170 locks with a movable contact segment of a microswitch 173 incorporated in the obturator 2 so that the microswitch 173 switches from off to on when the front end of the detection rod 170 touches to an organ in the body cavity.

A switch detection circuit 174 detects the on condition of the microswitch 173. An output signal sents out from the switch detection circuit 174 are supplied to the breaking circuit 158 and the alarm circuit 159.

The breaking circuit 158 responds to the signal from the switch detection circuit 174 and breaks the current circulation of power control circuit 121. The alarm circuit 128 responds to the signal from the switch detection circuit 174 and sends out visual or auditory alarm of light or sound.

Therefore, the modification switches the microswitch 173 from off to on when the detection rod 170 touches to the organ in the body cavity. In this case the switch detection circuit 174 sends out the signal to the breaking circuit 128 and the breaking circuit 128 responds. This breaks the high frequency current and alarm is sent out.

The obturator 2 shown in FIG. 55 has a pair of electrode 132a, 132b at the piercing tip 3. But a pair or plural pairs of bipolar electrodes 132a, 132b may be installed on the piercing tip 3 of the obturator 2 as shown in FIGS. 58a, 58b, 59a, 59b, 60a, 60b.

Figure 61:
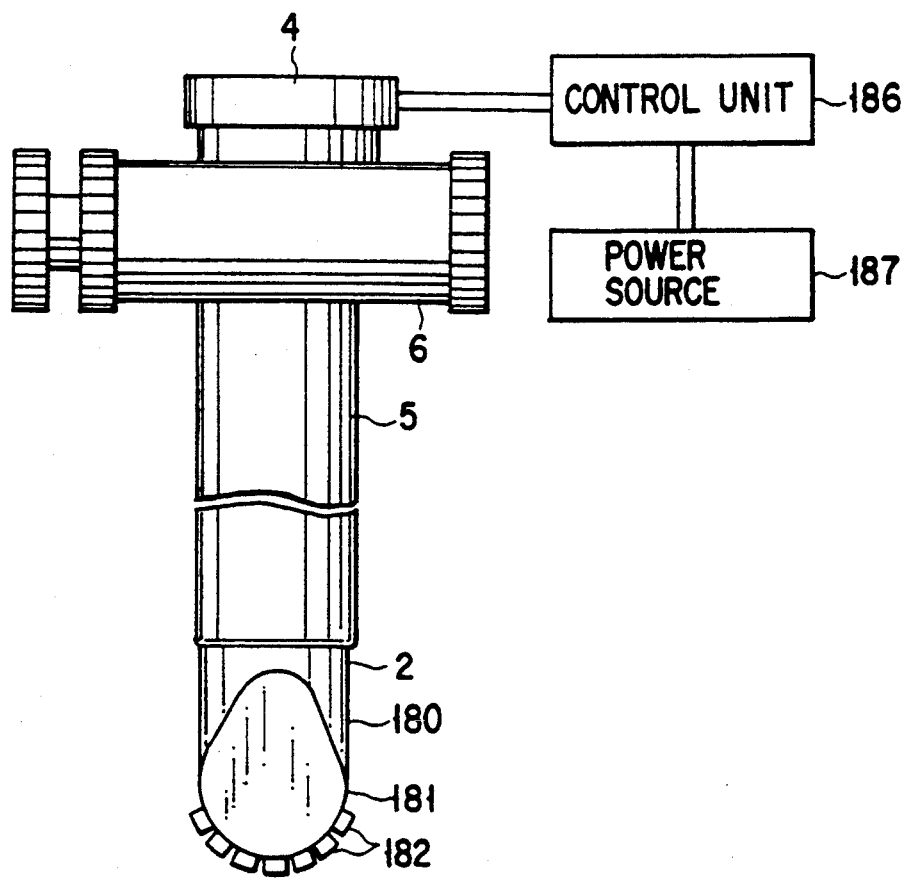
FIG. 61 is a drawing showing a twenty-first embodiment of the invention.

A twenty first embodiment of the invention is explained with FIG. 61 as a reference.

The obturator 2 is formed by installing wedge-shaped a front end 181 (corresponding to the piercing tip 3) with the front end formed in a circuit arc at the front end of a rod-shaped obturator body 180, and plural pieces of electrodes 182 are installed at the front end circular arc part of the front end 181 in a freely advancing and retreating way in the direction of the radius of the front end circular arc part. The obturator body 180 is formed with insulation materials.

Figure 62:
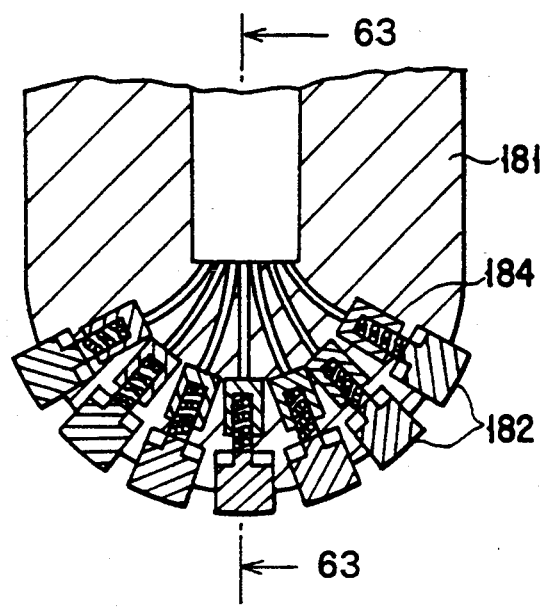
FIG. 62 is a sectional view showing the front end portion of the obturator shown in FIG. 61.

The electrodes 182 as shown in FIGS. 61, 62 and 63, are given force in the direction of radium projection from the front end of the obturator 2 by insulation springs 183 installed in the front end 181. The electrodes 182 retreat into the front end 181 against the force given by insulation the springs 183 when the front end 181 is pressed to the body 101 of the patient. Current is circulated to the electrodes 182 when they touch below-mentioned current circulation parts 184 installed in the front end 181. Each of these current circulation parts 184 is connected to a control unit 186 (FIG. 61) through lead lines 185 so that high frequency current is circulated from a power source unit 187 connected to the control unit 186. The current circulation parts 184 is formed cylinder shaped. The insulation springs 183 are contained inside of the cylinder shaped parts 184 in a freely expansionable and contractable way.

The control unit 186 controls the current circulation to each of electrodes 182. The control unit 186 detects values of the high frequency current circulated from the power source unit 186 to each electrodes 182. The control unit 186 is constructed so that once the current circulation to each electrode 182 stops each electrode 182, controls independently to prevent resumption of the current circulation unless in the case of resetting.

In this construction, when the front end 181 of the obturator 3 projected from the front end of the cannula 5 is pressed to the abdominal wall of the patient, the electrodes 182 retreat into the front end 181 of the obturator 2 against the force given by the insulation springs 183 and touch the current circulation parts 183. When the electrodes 182 touch the current circulation part 183, the high frequency current is supplied to the electrodes 182 through the control unit 186 and the current circulation parts 184 from the power source unit 187. This allows the tissue 101 incision with Joule heat generated at the electrodes 182 as shown in FIG. 64a.

Figure 64B:
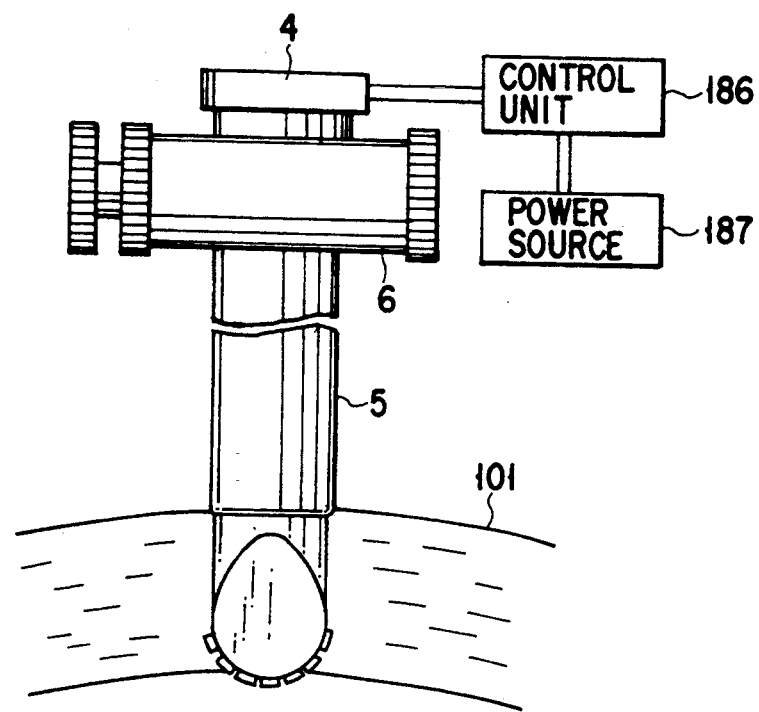
Figure 64C:
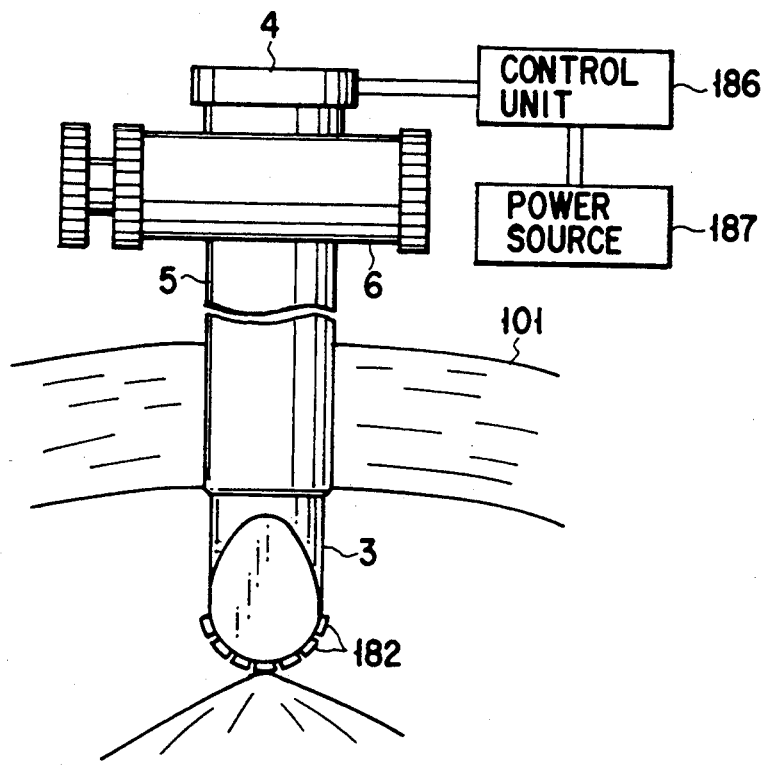

Moreover, as shown in FIG. 64b, when the front end 181 of the obturator 2 penetrates the tissue 101 and pierces in the body cavity, the electrodes 182 shift in the direction of projecting from the front end 181 of the obturator 2 and the current circulation to the electrodes 182 stops. In this case, the control unit 186 detects values of the high frequency current supplied from the power source 187 to the electrodes 182, and if it is known that the current circulation to the electrodes 202 is stopped, controls sequentially so that current circulation-stopped electrode 182 does not independently resume circulation.

Figure 65:
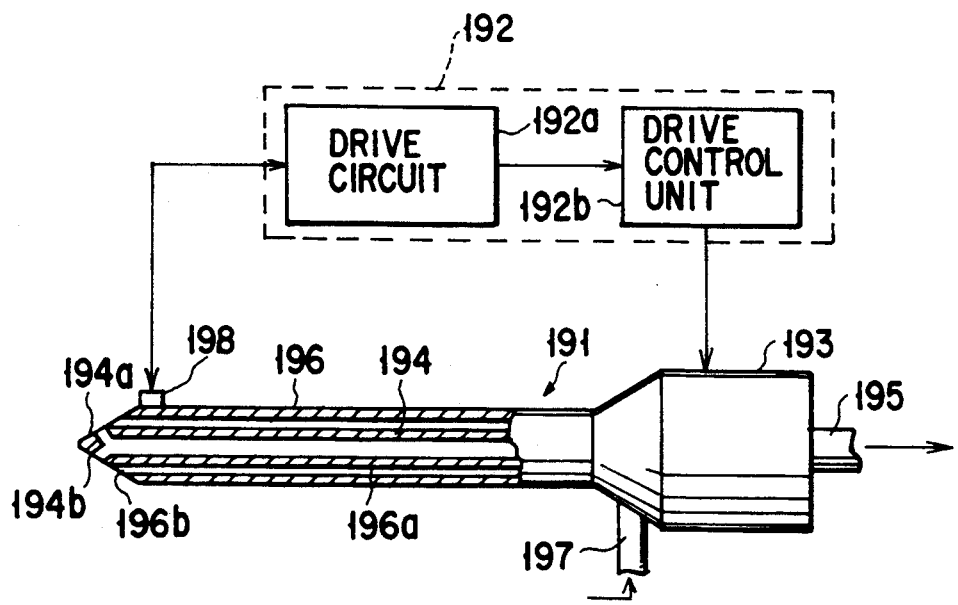
FIG. 65 is a drawing showing a twenty-second embodiment of the invention.
Figure 66:
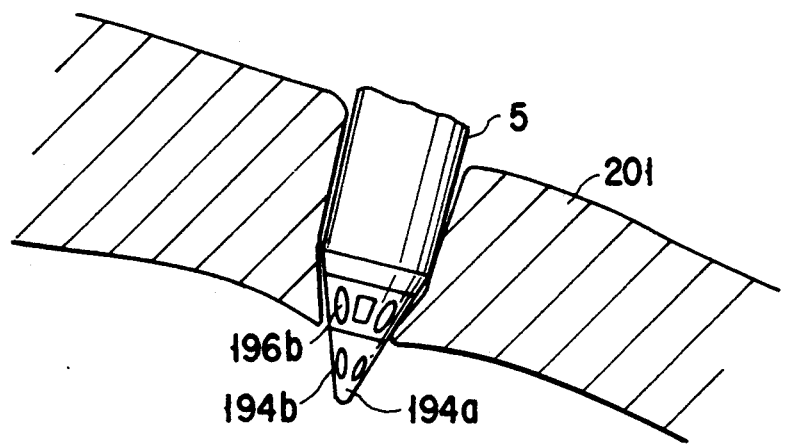
FIG. 66 is a drawing to explain the action of the obturator shown in FIG. 65.

FIGS. 65 and 66 explain a trocar of the type using supersonic waves or the so-called supersonic obturator device as a twenty second embodiment of the invention.

The supersonic obturator device comprises a suction probe 191, a drive device 192 for controlling drive of supersonic oscillator, and a suction water supply device (not illustrated) with built-in suction pin, suction pump, water supply tank and water supply pump.

The suction probe 191 has a probe body 193 with builtin supersonic oscillator (not illustrated) and a supersonic suction pipe 194 installed in protrusion from the probe body 193. The supersonic suction pipe 194 is formed in a long and narrow shape allowing insertion into the body cavity (e.g., the peritioneal cavity). The pipe 194 is formed of metal of good supersonic wave transmission efficiency, and is guided to the rear end side of the probe body 193. A flexible suction pipe line 195 is connected with the rear end side of the probe body 193. The supersonic suction pipe 194 is connected in continuous current connection with the suction pipe line 195.

An obtuse cone 194a is formed at the front end of the supersonic suction pipe 194. An opening 194b is formed at the cone 194a. This means that the opening 194b is in continuous current connection with a suction pipe line 195, and is connected with the suction pump described above through the suction pipe line 195 and section pin of the suction water supply device (not illustrated) described above.

Supersonic oscillation generated by the supersonic oscillator in the probe body 193 is transmitted to the supersonic suction pipe 194. The cone 194a of the supersonic suction pipe 194 transmits supersonic oscillation to the body wall.

A sheath 196 larger in diameter then the supersonic suction pipe 194 is connected with the front end side of the probe body 193. The sheath 196 has an outside diameter allowing insertion into the cannula 5, and forms a water supply pipe line 196a between the sheath 196 and the periphery of the supersonic suction pipe 194. The tip of sheath 196 is taper shaped like the cone 194a of the supersonic suction pipe 194, and water supply opening 196b is formed there. The water supply opening 196b is in continuous current connection with a water supply cap 197 that is connected with the side of the probe body 193. The water supply cap 197 is connected with the water supply pump of the suction water supply device through the water supply tank of the suction water supply device (not illustrated). This means that water comes out of the tip of the sheath 196 with the operation of the water supply pump.

A pressure sensor 198 is installed at the periphery of the tip of the sheath 196. The pressure sensor 198 detects pressure when the sheath 196 touches the body.

The drive device 192 is equipped with a drive circuit 192a that excites supersonic oscillator of the suction probe 191 through generation of high frequency current and generates supersonic waves from the supersonic oscillator, and a drive control circuit 192b that controls the drive of the drive circuit 192a in accordance with the output of the pressure sensor 198. The drive control circuit 192b stops the drive of the drive circuit 192a and stops excitation of the supersonic oscillator of the suction probe 191 when the pressure sensor 198 ceases sensing pressure from the body.

The following are explanations of the actions:

The operator installs the suction probe 191 of the supersonic obturator system on the cannula 5, and pierces it into the body 201 of the patient with pneumoperitoneum. When the pressure sensor 198 touches to the body 201, the drive control circuit 192b responds to pressure detection signals of the pressure sensor 198, and set the drive circuit 192a to operation. This excites the supersonic oscillator of the suction probe 191.

Supersonic oscillation generated by the supersonic oscillator is transmitted to the body 201 by the supersonic suction pipe 194, and the body 201 is emulsified gradually. The emulsified tissue is sucked into suction pin of the suction water supply system (not illustrated) through the supersonic suction pipe 194. At this time, water is supplied to tissue that is being emulsified through the water supply pipe line 196a of the sheath 196. The water supply accelerates suction of emulsified tissue and, at the same time, colls the supersonic suction pipe 194.

When the insertion of trocar cannula continues and the installation site of the pressure sensor 198 passes the body 201, the pressure sensor 198 ceases detecting pressure, the drive control circuit 192b responds to it, and the operation of the drive circuit 192a stops. As a result, oscillation of supersonic oscillator stops and supersonic oscillation transmission from the supersonic suction pipe 194 to the body 201 stops before the trocar cannula reaches the organ.

As described above, the supersonic suction operation stops automatically with the insertion of trocar cannula into the peritoneal cavity.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A trocar comprising:
   an obturator having a piercing tip for pinking in tissue; and,
   a cannula comprising a spirally coiled wire wherein each coil of said wire is wound to be adjacent to a next coil of said wire thereby forming a tube shaped coil, said cannula having a proximal open end, for forming a passage in the pinked in tissue pinked in by the piercing tip, thereby enabling an insertion of one of an endoscope and a surgical tool into a body cavity.

2. The trocar according to claim 1, further comprising a housing mounted on the proximal open end of the cannula.

3. The trocar according to claim 1, further comprising a waterproof resin layer formed on one of a periphery and an inner perimeter of the cannula.

4. The trocar according to claim 2, wherein said housing includes seal means for closing an inlet nozzle formed on the housing.

* * * * *